US009101276B2

(12) United States Patent
Georgopoulos

(10) Patent No.: US 9,101,276 B2
(45) Date of Patent: Aug. 11, 2015

(54) ANALYSIS OF BRAIN PATTERNS USING TEMPORAL MEASURES

(75) Inventor: Apostolos Georgopoulos, Minneapolis, MN (US)

(73) Assignee: REGENTS OF THE UNIVERSITY OF MINNESOTA, Minneapolis, MN (US)

(*) Notice: Subject to any disclaimer, the term of this patent is extended or adjusted under 35 U.S.C. 154(b) by 1792 days.

(21) Appl. No.: 11/825,509

(22) Filed: Jul. 6, 2007

(65) Prior Publication Data

US 2008/0091118 A1    Apr. 17, 2008

Related U.S. Application Data

(60) Provisional application No. 60/818,931, filed on Jul. 6, 2006, provisional application No. 60/851,599, filed on Oct. 13, 2006.

(51) Int. Cl.
| | |
|---|---|
| *A61B 5/0476* | (2006.01) |
| *A61B 5/04* | (2006.01) |
| *G06F 19/00* | (2011.01) |
| *A61B 5/0482* | (2006.01) |

(52) U.S. Cl.
CPC ........ *A61B 5/04008* (2013.01); *G06F 19/3437* (2013.01); *A61B 5/0476* (2013.01); *A61B 5/0482* (2013.01)

(58) Field of Classification Search
CPC ............................ A61B 5/0476; A61B 5/0482
USPC .................................................. 600/544, 545
See application file for complete search history.

(56) References Cited

U.S. PATENT DOCUMENTS

| 4,736,751 A | 4/1988 | Gevins et al. |
|---|---|---|
| 5,230,346 A | 7/1993 | Leuchter |

(Continued)

FOREIGN PATENT DOCUMENTS

| EP | 1995942 | 11/2008 |
|---|---|---|
| EP | 2024901 | 2/2009 |

(Continued)

OTHER PUBLICATIONS

Janeczko, C.; Lopes, H.S.; , "A genetic approach to ARMA filter synthesis for EEG signal simulation," Evolutionary Computation, 2000. Proceedings of the 2000 Congress on , vol. 1, no., pp. 373-378 vol. 1, 2000.*

(Continued)

*Primary Examiner* — Michael Kahelin
*Assistant Examiner* — Tho Tran
(74) *Attorney, Agent, or Firm* — Patterson Thuente Pedersen PA

(57) ABSTRACT

A set of brain data representing a time series of neurophysiologic activity acquired by spatially distributed sensors arranged to detect neural signaling of a brain (such as by the use of magnetoencephalography) is obtained. The set of brain data is processed to obtain a dynamic brain model based on a set of statistically-independent temporal measures, such as partial cross correlations, among groupings of different time series within the set of brain data. The dynamic brain model represents interactions between neural populations of the brain occurring close in time, such as with zero lag, for example. The dynamic brain model can be analyzed to obtain the neurophysiologic assessment of the brain. Data processing techniques may be used to assess structural or neurochemical brain pathologies.

15 Claims, 15 Drawing Sheets

(56) References Cited

U.S. PATENT DOCUMENTS

| | | | |
|---|---|---|---|
| 5,632,276 A | 5/1997 | Eidelberg | |
| 5,873,823 A | 2/1999 | Eidelberg | |
| 6,061,593 A * | 5/2000 | Fischell et al. | 600/544 |
| 6,195,576 B1 * | 2/2001 | John | 600/409 |
| 6,463,321 B2 | 10/2002 | Granger | |
| 6,561,992 B1 | 5/2003 | Eberhart | |
| 6,687,525 B2 | 2/2004 | Llinas et al. | |
| 6,741,888 B2 | 5/2004 | Musha | |
| 6,947,790 B2 * | 9/2005 | Gevins et al. | 600/544 |
| 7,177,675 B2 | 2/2007 | Suffin et al. | |
| 7,499,894 B2 | 3/2009 | Marom et al. | |
| 7,860,561 B1 * | 12/2010 | Modarres | 600/544 |
| 2003/0105409 A1 * | 6/2003 | Donoghue et al. | 600/545 |
| 2004/0068199 A1 * | 4/2004 | Echauz et al. | 600/544 |
| 2004/0133119 A1 * | 7/2004 | Osorio et al. | 600/544 |
| 2005/0038669 A1 * | 2/2005 | Sachdeva et al. | 705/2 |
| 2006/0015034 A1 | 1/2006 | Martinerie et al. | |
| 2006/0036297 A1 * | 2/2006 | Seidman | 607/55 |
| 2006/0111644 A1 * | 5/2006 | Guttag et al. | 600/544 |
| 2006/0135879 A1 * | 6/2006 | Liley | 600/544 |
| 2006/0149160 A1 * | 7/2006 | Kofol et al. | 600/544 |
| 2009/0036791 A1 * | 2/2009 | Plenz | 600/544 |
| 2009/0082688 A1 | 3/2009 | Wagner | |
| 2009/0297000 A1 | 12/2009 | Shahaf et al. | |
| 2009/0326404 A1 * | 12/2009 | Sajda et al. | 600/544 |
| 2011/0004115 A1 | 1/2011 | Shahaf et al. | |
| 2011/0004412 A1 | 1/2011 | Shahaf et al. | |
| 2011/0022548 A1 | 1/2011 | Shahaf et al. | |
| 2011/0190621 A1 | 8/2011 | Verdoorn et al. | |

FOREIGN PATENT DOCUMENTS

| | | |
|---|---|---|
| WO | WO 03/005899 | 1/2003 |
| WO | WO2007/138579 | 12/2007 |
| WO | WO2009/069135 | 6/2009 |
| WO | WO2011/086563 | 7/2011 |

OTHER PUBLICATIONS

David et al., Evaluation of different measures of functional connectivity using a neural mass model, NeuroImage Journal, vol. 21(2), Feb. 2004, pp. 659-673.*

Nam et al., Independent Component Analysis of Ictal EEG in Medical Temporal Lobe Epilepsy, Epiplesia vol. 43 No. 2: pp. 160-164, 2002.*

Berendse, Hank W., "Magnetoencephalographic studies in Parkinson's disease", New Approaches to the clinic use of MEG. VUMC, Amsterdam. Presentation Slides. Mar. 27, 2006.

Cover, Keith S., "Can MEG be used to monitor Multiple Sclerosis?", VU University Medical Centre, Amsterdam. Presentation Slides.

Stam, C.J., "Magnetoencephalographic studies in Alzheimer's disease", New Approaches to the clinic use of MEG. VUmc, Amsterdam. Presentation Slides. Mar. 27, 2006.

Stam, C.J., "Use of Magnetoencephalography to assess resting state Functional Connectivity in Neurological Disease" VU University Medical Centre, Amsterdam. 28th International Congress of Clinical Neurophysiology, Edinburgh, Scotland. Sep. 11, 2006.

Kohn et al, "$^{99m}$Tc-HMPAO SPECT Study of Cerebral Perfusion After Treatment with Medication and Electoconvulsive Therapy in Major Depression", The Journal of Medicine, vol. 8, No. 8. pp. 1273-1278.

Gross et al, "Dynamic imaging of coherent sources: Studying neural interactions in the human brain", PNAS. vol. 98. No. 2. Jan. 16, 2001. pp. 694-699.

Habeck et al, Abstract. "A New Approach of Spatial Convariance Modeling of Functional Brain Imaging Data: Ordinal Trend Analysis", Neural Computation. vol. 17, Issue 7. Jul. 2005.

International Search Report for International Application No. PCT/US2007/015545 dated Jul. 2, 2008.

Written Opinion of the International Search Authority for International Application No. PCT/US2007/015545 dated Jul. 2, 2008.

Stark, et al, "Partial Cross-Correlation Analysis Resolves Ambiguity in the Encoding of Multiple Movement Features", The American Physiological Society. 2006.

Magnetoencephalography and Neuromagnetic Signals. Chapter 1. pp. 8-16.

Leuthold et al., "Time series analysis of magnetoencephalographic data during copying" Exp Brain Res (2005) 164:411-422.

Stam et al. "Magnetoencephalographic evaluation of resting-state functional connectivity in Alzheimer's disease". 2006 NeuroImage 32:1335-1344.

Langheim et al., "Synchronous dynamic brain networks revealed by magnetoencephalography", 2006 Proc. Natl. Acad. Sci. USA. 103 455-459.

Sajda, Paul, "Machine Learning for Detection and Diagnosis of Disease" Ann. Rev.Biomed. Eng. 8: 537-565.

Abasolo et al., "Entropy analysis of the EEG background activity in Alzheimer's disease patients". 2006. Phys. Measurement 27: 241-253.

Jeong, "EEG dynamics in patients with Alzheimer's diease". 2004 Clin. Neurophys. 115:1490-1505.

Rabinovici et al., Distinct MRi atrophy patterns in autopsy-proven Alzheimer's disease and frontotemporal lobar degeneration. Am J. Alzheimers Dis. Other. Demen. 2007. 22: 474-488.

Diamond et al., Relationship of fMRI activation to clinical trial memory measures in Alzheimer's disease. 2007. Neurology 69:1331-1341.

Kinkingnehun et al., VBM anticipates the rate of progression of Alzheimer disease: 3-year longitudinal study.2008. Neurology. 70: 2201-2211.

Georgopoulos, et al., 2007. "Synchronous neural interactions assessed by magnetoencephalography: a functional biomarker for brain disorders". J Neural. Eng. 4:349-355.

Kloppel et al., 2008. Automatic classification of MR scans in Alzheimer's disease. Brain 131:681-689.

Jack, et al. $^{11}$C PiB and structural MRI provide complementary information in imaging Alzheimer's disease and amnestic mild cognitive impairment. Brain 131:665-680.

Greicius, et al., 2004. Default-mode network activity distinguishes Alzheimer's disease from healthy aging: Evidence from functional MRI. Proc. Natl. Acad. Sci. USA 101:4637-4642.

Sorg, et al., 2007. Selective changes of resting-state networks in individuals at risk for Alzheimer's disease. Proc. Natl. Acad. Sci. USA 104: 18760-18765.

Lehmann, et al., 2007. Application and comparison of classification algorithms for recognition of Alzheimer's disease in electrical brain activity (EEG). J Neurosci. Methods 161:342-350.

Stam et al., 2007. Small-world networks and functional connectivity in Alzheimer's disease. Cerebral Cortex 17:92-99.

Fernandez, et al., 2006. Quantitative magnetoencephalography of spontaneous brain activity in Alzheimer disease. An exhaustive frequency analysis. Alz. Dis. Assoc. Disord. 20:153-159.

Criado, et al., Using magnetoencephalography to study patterns of brain magnetic activity in Alzheimer's disease. Am J Alzheimers Dis. Other Demen. 21:416-423.

Dehaan, et al., 2008. Resting-state oscillatory brain dynamics in Alzheimer disease. J Clin. Neurophys. 25: 187-193.

Uhlhass, et al., 2006. Neural Synchrony in brain disorders: Relevance for cognitive dysfunctions and pathophysiology. Neuron 52: 155-168.

Ressom, et al., 2008. Classification algorithms for phenotype prediction in genomics and proteomics. Front. Biosci. 13:691-708.

Tan et al., 2006 Neural mechanisms of movement tau: a magnetoencephalographic (MEG) study Soc of Neurosci.

Leuthold et al., (2005b) Synchronous dynamic brain interactions in alcoholism: A longitudinal magnetoencephalographic (MEG) study during withdrawal. Soc Neurosci Abstr 110: 17.

Koutlas et al., 2006 Neural mechanisms of tactile sensibility studied using magnetoencephalography (MEG): time-frequency analysis. Soc Neurosci.

Langheim et al., 2004 Motor Trajectory from Magnetoencephalographic (MEG) Data. Soc Neurosci Abstr 884.1.

Dumas et al., 2005 Magnetoenephalographic (MEG) Signals Predict Music Soc Neurosci Abstr 975.10.

(56) References Cited

OTHER PUBLICATIONS

Langheim et al., 2004 Interactions between magnetoencephalographic (MEG) Signals as Revealed by Time Series Analysis. Soc Neurosci Abstr 884.3.

Langheim, et al., 2002 Dynamic Brain Interactions Revealed by magnetoencephalography (MEG). Soc. of Neuroscience.

McCarten et al., (2005) MEG in elderly subjects and in subjects with mild cognitive impairment (MCI) and Alzheimer's disease (AD). 2. Negative synchronous dynamic interactions. Soc. Neurosci. Abstr. 542: 7.

Lewis et al., (2005) Magnetoencephalography (MEG) in elderly subjects and in subjects with mild cognitive impairment (MCI) and Alzheimer's disease (AD). 1. Positive synchronous dynamic interactions. Soc Neurosci Abstr 542: 6.

Dumas et al., 2006 Neural mechanisms of pitch perception studied using magnetoencephalography (MEG) Soc Neurosci.

Koutlas et al., 2005 Hierarchical tree clustering AF areas activated during tactile stimulation: A MEG Study. Soc Neurosci.

Merkle et al., 2006 Hierarchical clustering of magnetoencephalographic (MEG) data. Soc Neurosci.

Karageorgiou et al., 2006 Linear discriminant classification analysis of synchronous neural interactions assessed by magnetoencephalography. Soc Neurosci.

Application and File History for U.S. Appl. No. 13/019,135, filed Feb. 1, 2011, inventors Verdoorn et al.

Independence (probability theory); Wikipedia. 4 pages. Last modified Jun. 7, 2012.

White Noise; Wikipedia. 8 pages. Last modified Jun. 15, 2012.

\* cited by examiner

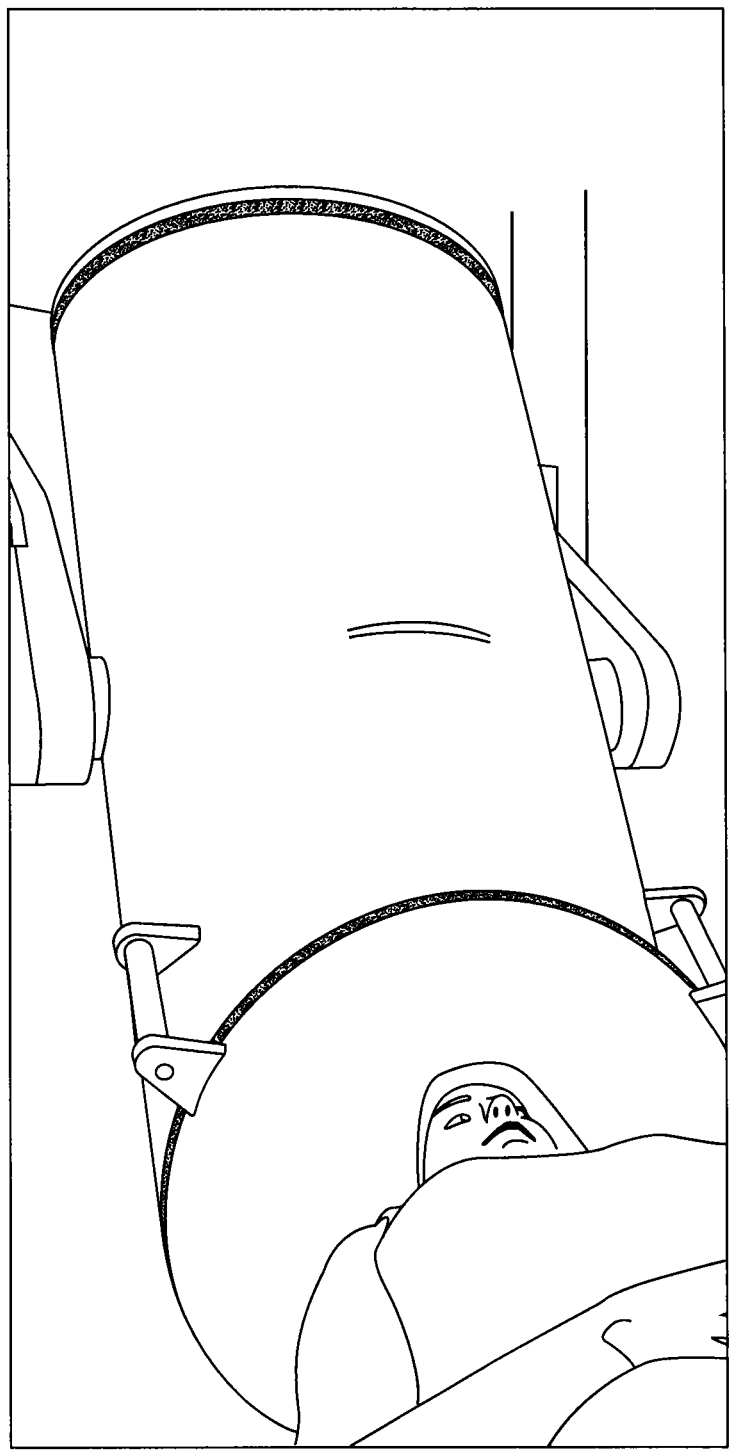
FIG. 1  -MEG Instrument

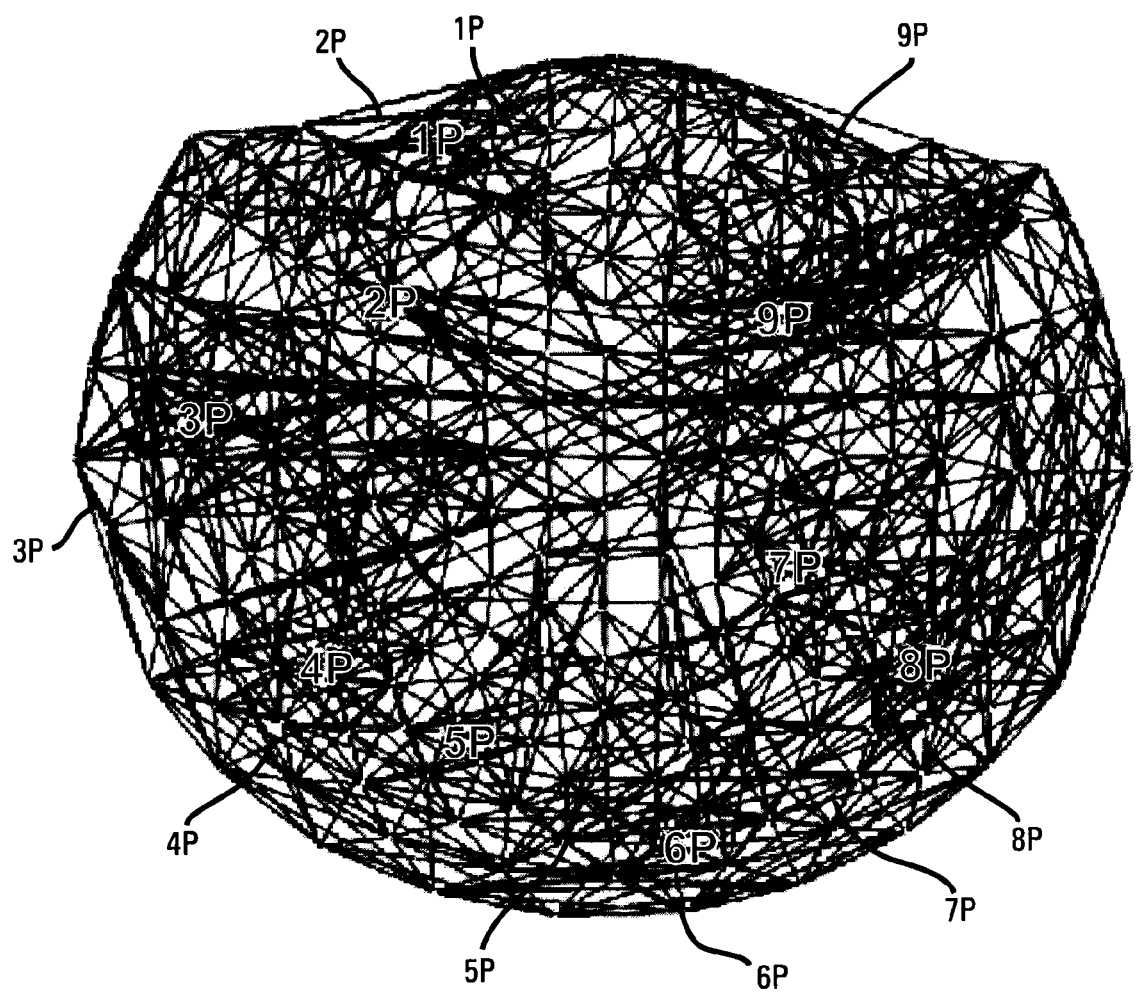
FIG. 6  Positive Coupling

Negative Coupling

ANALYSIS OF BRAIN PATTERNS USING TEMPORAL MEASURES

RELATED APPLICATIONS

This application claims the benefit of U.S. Provisional Application No. 60/818,931, filed Jul. 6, 2006, and entitled "CLASSIFICATION AND QUANTITATIVE ASSESSMENT OF BRAIN PATTERNS USING MAGNETO-ECEPHALOGRAPHY;" and U.S. Provisional Application No. 60/851,599 Filed Oct. 13, 2006, and entitled "CLASSIFICATION AND QUANTITATIVE ASSESSMENT OF BRAIN PATTERNS USING MAGNETOECEPHALOGRAPHY," both of which are incorporated by reference herein in their entirety.

GOVERNMENT SUPPORT

This invention was made with Government support under award DE-FG02-99ER62764 awarded by the Department of Energy to the MIND Institute and with support by the US Department of Veterans Affairs. The Government has certain rights in this invention.

TECHNICAL FIELD

This document pertains generally to neurophysiologic analysis, and more particularly, but not by way of limitation, to analysis of brain patterns using time series representation.

BACKGROUND

Like any other organ of the body, the function of the brain needs to be assessed to evaluate its status in health and disease. However, unlike any other organ of the body, no good tests of brain function are available. Typical behavioral examinations include standard neurological examination, psychiatric interview, or neuropsychological testing. The electroencephalogram (EEG) provides little information unless there is major epilepsy or severely disordered brain function, as in comatose states. Methods for assessing brain structure (such as magnetic resonance imaging, MRI), chemistry (magnetic resonance spectroscopy, MRS), fluorodeoxy-glucose based positron emission tomography (PET), or pharmacology (ligand-based PET) do not and cannot substitute for assessing brain function. Finally, "functional" MRI (fMRI) and $O^{15}$—based-PET are concerned with brain areas activated in specific tasks and not about brain function per se.

Neurological disease, including for example, cognitive impairment, is a huge and growing problem. For example, in the case of the cognitive impairment known as Alzheimers disease (AD), effective intervention depends on early recognition. The amnestic form of mild cognitive impairment (MCI) is a predementia syndrome in older adults that often evolves into AD. While the clinical characterization of AD and mild cognitive impairment is usually accurate, misdiagnoses do occur, complicating research and treatment efforts.

An objective test for AD, cognitive impairment, or other neurological conditions would be desirable, but the various approaches proposed to-date have significant drawbacks, limiting their potential for application as a sensitive, reliable, diagnostic or evaluative tool.

For instance, one type of approach, as exemplified by U.S. Pat. No. 6,463,321, utilizes electroencephalogram (EEG) measurements during evoked response potential (ERP) trials. Data collected from the EEG sensors are aggregated, and a single vector representing the overall subject response to the ERP trials is produced. This vector is then compared against those of known healthy subjects and subjects with diagnosed neurological disorders, such as AD, depression, or schizophrenia. One drawback of ERP-based measurements is the evoked response to the stimulus causes certain brain regions to become very active while other brain regions remain relatively inactive. Consequently, the aggregated EEG measurements represent primarily the activated brain regions. Using this approach, a measurement representing overall brain activity, taking into account the activity of less active regions, is not possible. This problem is exacerbated by the use of conventional EEG instrumentation, which tends to detect primarily electrical activity near the outer surface of the brain, with substantially reduced sensitivity at deeper brain regions.

U.S. Pat. No. 7,177,675 discloses an approach for selecting therapies for patients diagnosed according to comparison to a database of symptomatic individuals who have had positive responses to various therapies. Quantitative neurophysiologic information such as that obtained by EEG/QEEG/MEG is compared against database records of the reference individuals to predict which course of treatment works best for someone with similar EEG/QEEG/MEG activity. However, the measurement and data analysis approaches disclosed involve mainly spectral analysis and are not capable of recognizing subtle characteristic indicia of certain diseases or conditions from among all of the measurements collected. Instead, the EEG/QEEG/MEG data, as a whole, is clustered according to treatment outcome.

In Leuthold et al., Time Series Analysis of Magnetoencephalographic Data, Exp. Brain Res., 2005, the authors describe experiments in which MEG data was acquired while subjects performed various motor tasks and experienced a variety of visual stimulation, including seeing changing images during an eye fixation task. Time domain ARIMA Box-Jenkins modeling was used to analyze the MEG data over short-term interactions of −25 to +25 ms. The data was pre-whitened, and pair-wise interactions between series of data obtained from the MEG were analyzed using a cross correlation function (CCF), an autocorrelation function (ACF) and a partial autocorrelation function (PACF). Hand movements and eye movements were monitored closely and used to relate the MEG output to the subject activity taking place. The sampling period was slightly above 1 kHz.

This work assessed the interactions between time series in pairs of sensors. Positive and negative cross-correlation patterns were observed for selected individual pairs of sensor outputs during the performing of the tasks by the subject. While this work produced some interesting insights into measurement techniques for taking MEG readings (such as the advantageous use of 1 kHz sampling, and preprocessing of the data to pre-whiten it), this work explored only individual sensor signal interactions, and did not take into account whole brain modeling in which large numbers of sensor groupings must be studied. Indeed, for reasons that will become apparent from the following disclosure, the disclosure of Leuthold et al. does not enable analyzing brain activity for purposes of characterizing a brain condition of a subject or making a diagnosis of a brain condition.

In view of these, and other drawbacks of known techniques, a practical solution is needed for automatically analyzing brain activity with the capability of reliably detecting and identifying significant neural patterns characteristic of certain conditions of interest for a variety of different subjects.

SUMMARY OF THE INVENTION

One aspect of the invention is directed to analyzing and classifying neurophysiologic activity of a subject, such as a human subject of research or study, or a psychiatric patient, for example. A set of subject data representing a time series of neurophysiologic activity acquired by a multiplicity of spatially distributed sensors arranged to detect neural signaling in the subject during an eyes-open idle state is received as input. The subject data can be acquired by a magnetoencephalogram measurement or some other suitable measurement that provides time series information and sufficient measurement sensitivity.

A plurality of templates classified according to various brain conditions are stored in a data store, such as a database, for example. Each of the templates represents selected subsets of statistically-independent temporal measures among neural populations measured from at least one other subject known to present a given brain condition. The statistically-independent temporal measures can include a set of partial cross correlations among groupings of different time series within the set of subject data representing generally synchronous interactions between neural populations in the subject's brain, for example.

The set of subject data is processed to obtain a dynamic model that represents temporal measures among neural populations in the subject. The dynamic model is dynamic in the sense that it represents the temporal measures as a function of time. In one example embodiment, the dynamic model includes partial cross-correlations of pairs of time series taken from the subject data. The dynamic model can include all pairs, or some subset of all of the pairs of time series.

A comparison is made of at least a portion of the dynamic model with the plurality of templates to produce a classification of neurophysiologic activity of the subject when the dynamic model corresponds with at least one of the plurality of templates.

In another aspect of the invention, neurophysiologic activity of a subject is analyzed by a system that includes a data input and a processor. The data input can include a communication interface such as a computer network interface, for example. The data input receives a set of subject data representing a time series of neurophysiologic activity acquired by each of a multiplicity of spatially distributed sensors arranged to detect neural signaling in the patient. The processor is communicatively coupled to the data input and programmed to process the set of subject data to obtain a dynamic brain model that represents statistically-independent temporal measures among neural populations in the subject's brain. The system can then analyze the dynamic brain model to estimate a neurophysiologic condition of the subject.

Another aspect of the invention is directed to a system for analyzing neurophysiologic activity of a first subject. The system includes a data input that receives sets of brain activity data corresponding to an eyes open idle state, such as an eye fixation task, each set representing a time series of neurophysiologic activity acquired by a multiplicity of spatially distributed sensors arranged to detect neural signaling in a corresponding subject; and a processor communicatively coupled to the data input.

The processor is programmed to process each set of brain activity data to produce a corresponding dynamic model of neural activity representing time-dependent coupling between neural populations of the first subject, including processing the brain activity data to produce a prewhitened time series having a characteristic of stationarity of mean, variance, and autocorrelation; computing pairwise, partial cross correlations of the prewhitened time series to produce estimates of strength and sign of signaling between pairs of the multiplicity of sensors representing pairwise interactions of neural populations; and performing a classification of the partial cross correlations to produce a measure of correlation of the brain activity data to validated reference data corresponding to a plurality of different neurophysiologic conditions.

Embodiments of the invention include diagnostic tools for use in clinical settings, or tools for evaluating subjects in research settings. More generally, aspects of the invention provide tools for automatically obtaining a neurophysiologic assessment of structural or neurochemical brain pathologies utilizing a data processing system. Systems and methods according to various aspects of the invention are useful for monitoring a potentially changing neurophysiologic condition of a subject, such as a progression of a disease, for example. Additionally, aspects of the invention provide solutions for monitoring treatment effectiveness of patients.

Moreover, aspects of the invention are useful for providing an automated neurophysiologic classification of a subject's brain condition from among a diverse set of conditions, known or unknown. For instance, embodiments of the invention can be used for providing accurate, differential classification from among one or more of the following conditions: a normal condition, Alzheimer's Disease, pre-dementia syndrome, mild cognitive impairment, schizophrenia, Sjögren's Syndrome, alcoholism, alcohol impairment, fetal alcohol syndrome, multiple sclerosis, Parkinson's Disease, bipolar disorder, traumatic brain injury, depression, autoimmune disorder, a neurodegenerative disorder, pain, a disease affecting the central nervous system, or any combination thereof.

Advantageously, embodiments of the invention may enable obtaining the brain characterization, diagnosis, and other results from a single trial, or measurement session, which may last only a few minutes or less. This offers a relatively low cost and high throughput for the use of measurement equipment that collects the data from subjects. For subjects, the comfort of short, non-invasive data collection sessions such as using MEG instruments, is a clear advantage over having to make multiple trips to the clinic or having to endure lengthy testing. Embodiments of the invention may overcome the disadvantages of the qualitative and subjective evaluations of brain disorders that are commonplace today with current indirect diagnostic techniques based on observation and other clinical data by providing a quantitative, statistically correlated measure of multiple brain conditions. Another benefit offered by aspects of the invention is the ability to accept as input non-preprocessed data. Thus, standard measurement instrument output can be utilized without the need for special equipment upgrades, and a subject can be fully evaluated for a variety of conditions without any a priori anticipation, or preparation for screening of certain hypothesized or speculated conditions.

The invention provides a variety of other advantages, which will become apparent from the following disclosure.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 1 illustrates an exemplary MEG instrument.

FIGS. 6-9B illustrate various examples of massively interconnected networks.

Figure 2A:
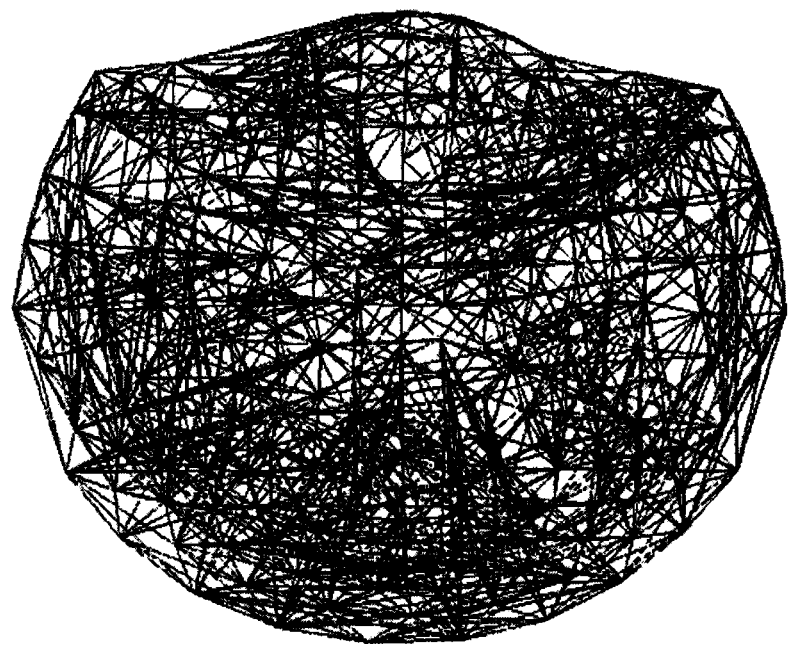
FIGS. 2A and 2B illustrate synchronous dynamic networks from a subject in a as a visual representation.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims and their equivalents.

DETAILED DESCRIPTION

The following detailed description includes references to the accompanying drawings, which form a part of the detailed description. The drawings show, by way of illustration, specific embodiments in which the present subject matter may be practiced. These embodiments, which are also referred to herein as "examples," are described in enough detail to enable those skilled in the art to practice the present subject matter. The embodiments may be combined, other embodiments may be utilized, or structural, logical and electrical changes may be made without departing from the scope of the present subject matter. The following detailed description is, therefore, not to be taken in a limiting sense, and the scope of the present subject matter is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Applications of Magnetoencephalography

Biomagnetism refers to the measurement of magnetic fields from sources within the body. These fields are produced by magnetic materials or ionic currents associated with biological activity. One example of physiological recording includes the human heart and an induction coil or other instruments as a detector. Other examples of biomagnetism include the study of the digestive system by following the motion of magnetic particles, and the measurement of magnetic contaminants in the lungs of metal workers. Some applications involve measurement of human brain activity. An example of a detector of magnetic fields includes a superconducting device called the SQUID (Superconducting Quantum Interference Device). The SQUID, along with its associated feedback electronics, is treated as a black box which provides an output voltage proportional to the magnetic flux applied to its detection coil. Magnetic signals are largely unaffected by passage through soft tissue and bone, while electrical signals are conducted by soft tissue and isolated by bone.

In one example, the detector includes a helmet design configured for "whole head" analysis and can include more than 100 SQUID channels. In one example, 248 channels are used, however more or fewer number of channels are also contemplated in accordance with various embodiments. When a group of neurons (for example, 10,000 or more), are activated together, the magnetic field produced by the net current may be detected by these coils. Using these measurements with assumptions about the distribution of neuronal activity, the location of the activity can be calculated. In one example, magnetoencephalography is currently used clinically primarily for pre-surgical mapping.

Magnetoencephalography is a functional imaging tool and an anatomical overlay from MRI or CT can be used to visualize the location of measured activity on the cortical surface. Magnetoencephalography has temporal resolution in the millisecond range and spatial accuracy of a few millimeters for sources not more than 3 cm deep. There are two types of MEG detection coils in use today for brain recordings: magnetometers and axial gradiometers. Magnetometers record the instantaneous level of the magnetic field at any time for a given spatial location. Gradiometers measure flux gradients, or spatial derivatives, of the local magnetic field for a given time-point. Gradiometers tend to be more sensitive to deeper thalamic sources; while magnetometers capture mostly cortical sources.

Traditional analyses of the MEG signal has centered on magnetic source localization (to identify and localize in the brain single or multiple virtual dipoles that explain a good percentage of the variance observed in the actual recordings). Other analysis of the MEG signal have been directed to distributed source modeling to derive estimates of current density in specific brain regions of interest. FIG. 1 illustrates a conventional magnetoencephalogram (MEG) instrument.

According to one embodiment of the present invention, MEG is used to study the dynamic short-term interactions (−25 to +25 ms) between prewhitened signals from human cortex recorded from 248 axial gradiometers during a 45 sec visual fixation task in elderly normal, MCI and AD subjects. As noted with positive correlations, it has been found that there is a significant increase in the strength of negative correlations with age that was accentuated in MCI and again in AD. Furthermore, MCI and particularly AD, are associated with new negative correlations not seen in normal subjects. Negative correlations usually imply feedback through interneurons linking neuronal pools. In the present study, negative correlations are seen at millisecond intervals between diverse and widely separated regions of brain, and these correlations intensified with age and expanded in MCI and AD. The brief interval is incompatible with activation of interneurons, and it is also unlikely that opposite reactions occur simultaneously to the same stimulus. It appears that these negative correlations are a normal part of the background synchronicity of neuronal systems, and that their increase reflects increasing neuronal synchronicity at the expense of the desynchronized activity, or degrees of freedom, necessary for neuronal processing.

Example 1

Magnetoencephalography (MEG) can be used in elderly subjects and in subjects with MCI and AD.

In one example, a fixation task and MEG are used to assess the dynamic status or dynamic function of the brain in three groups of elderly subjects (77.1±1.5 y, mean±SEM, N=1 1): normal (N=4, 76.5±2.1 y), subjects with MCI (N=4, 75.7±3.7 y), and subjects with AD (N=3, 79.7±0.3 y). Data is acquired from 248 axial gradiometers (Magnes 3600 WH, 4-D Neuroimaging) while subjects fixate on a spot for 45 s, and were preprocessed to remove cardiac artifacts or eye blink artifacts.

After prewhitening the time series by fitting an AutoRegressive Integrative Moving Average (ARIMA) model and taking the residuals, all pairwise, zero-lag, partial cross correlations are calculated, providing estimates of the strength and sign (positive, negative) of direct synchronous coupling between neuronal populations at 1 ms temporal resolution.

An analysis of covariance is performed in which the positive partial correlation is the dependent variable, the group and the sensors are fixed factors, and the age and the intersensor distance are covariates. A highly statistically significant effect of the group ($p<10^{-12}$ F test) is revealed. Pairwise comparisons using the Bonferroni correction shows that the normal and MCI groups do not differ significantly from one another (p=0.23) but the AD group has significantly lower average partial correlation than either the normal ($p<10^{-7}$)r the MCI group ($p<10^{-11}$) Synchronous positive neural interactions in AD appear reduced in strength.

In one example, an analysis of covariance is performed in which the negative partial correlation is the dependent variable, the group and the sensors are fixed factors, and the age and the intersensor distance are covariates. A highly statistically significant effect of the group ($p<10^{-6}$, F test) is revealed. Pairwise comparisons using the Bonferroni correction shows that the normal and MCI groups do not differ significantly from one another (p=0.23) but the AD group has significantly less negative average partial correlation than either the normal ($p<10^{-4}$) or the MCI group ($p<10^{-6}$). The changes are in the same direction (i.e. lower correlations) as those found for the positive interactions. Synchronous neural interactions in AD appear reduced in strength.

Interactions among neural populations underlie all brain functions, from sleep and wakefulness to higher cognitive processes. One aspect of the invention recognizes that evaluating the strength and spatial patterns of these interactions can contribute substantially to the understanding of brain function and its relations to behavior.

One aspect of the invention is directed to synchronous neural interactions (SNI) by which to assess dynamic brain function at high temporal resolution using magnetoencephalography (MEG). The technique according to one embodiment includes measurement of dynamic synchronous interactions among neuronal populations which correspond to brain function. Embodiments of the invention can be used for providing accurate, differential classification from among one or more of the following conditions: a normal condition, Alzheimer's Disease, pre-dementia syndrome, mild cognitive impairment, schizophrenia, Sjögren's Syndrome, alcoholism, alcohol impairment, fetal alcohol syndrome, multiple sclerosis, Parkinson's Disease, bipolar disorder, traumatic brain injury, depression, autoimmune disorder, a neurodegenerative disorder, pain, a disease affecting the central nervous system, or any combination thereof.

One method facilitates demarcation of ranges for healthy subjects, classifications for disease groups, measures of severity or degree with which a certain condition is manifested in a subject, and allows monitoring of changes in brain function coincident with disease progression or therapy intervention. In one example, the method can be used routinely for assessing dynamic brain function and aids in differential diagnosis and monitoring the effects of intervention. In one example embodiment, classification scores and posterior probabilities are obtained by which to quantify the severity of brain dysfunction and monitor its course and the effect of treatment.

The method includes analysis of MEG data by way of dynamic, synchronous interactions among neuronal populations. The method can be used to discriminate between various brain impairments, including but not limited to subjects with AD, chronic alcoholism, MCI, multiple sclerosis, schizophrenia, and Sjögren's syndrome. The present subject matter can be used as a test for assessing dynamic brain function and serve as an aid in differential diagnosis.

In one example embodiment of the present invention, time series analysis methods are applied to the MEG signal to estimate dynamic, moment-to-moment interactions between neuronal populations to predict motor behavior and music to derive synchronous neural networks involved in a task, and to assess their alteration in AD and chronic alcoholism. This time series analysis approach has proven very useful and promising for evaluating the status of brain function.

In one example embodiment of the present invention, time series analyses is used to derive synchronous dynamic networks from single trials, unaveraged and unsmoothed, recorded simultaneously from 248 MEG sensors at 1 ms temporal resolution during an eye fixation task using the cross correlation function (CCF). This analysis yields visualizations of synchronous dynamic brain networks that are very similar and robust across healthy subjects. The high density spatial sampling, the dynamic nature of the networks uncovered, and the robustness indicate utility as a test for assessing dynamic brain function at rest.

Statistically significant differences are noted in these networks between healthy subjects and subjects with AD, or MCI, as well as in chronic alcoholics during detoxification. In addition, CCF estimates of regional connectivities exhibit discriminatory power sufficient to classify individual subjects to particular groups (e.g. healthy, AD, MCI). Furthermore, genetic searching algorithms allow extension of this classification system to additional groups, including schizophrenia and chronic alcoholism.

Genetic searching algorithms, or genetic algorithms (GA), have been developed to find genes in large arrays of chromosomes. A genetic algorithm is used in some embodiments of the present invention to search the large set of synchronous interactions (for example, 30,628 when using 248 sensors) to find subset of these synchronous interactions that are able to predict the classifications of brain diseases and conditions.

Example 2

Methodology

The subject lies supine on a bed and is instructed to look at a spot in front of them for 1 minute. The subjects are asked to keep their eyes fixated on the spot and not to blink. Then they close their eyes for 3 more minutes, and this is the end of the test. MEG data from the fixation period are used for all analyses. In one embodiment, the data acquired during the eyes closed condition are useful for identifying and removing signal artifacts, such as the cardiac artifact.

MEG Instrument Data is acquired using the MEG instrument. Subjects lie on a bed in the magnetically shielded room and MEG signals are acquired from 248 axial gradiometers (0.1-400 Hz, sampled @ 1017 Hz, Magnes 3600 WH, 4-D Neuroimaging, San Diego, Calif.) during the whole duration of the experiment (~4 min).

Data Analysis

Data Preprocessing.

Cardiac artifacts may be removed using an event-synchronous subtraction method. Due to the very short duration of the eye-fixation period (1 min), artifacts from eye blinks are not anticipated, but if present can be detected and removed or blanked from the data.

Time Series Modeling of the MEG Data.

Analysis of single-trial, unaveraged data, following removal of the cardiac and/or eye blink artifacts benefits from the high temporal resolution and dynamic variation inherent in the MEG signal in order to assess functional interactions among large neuronal populations in a given task by calculating all cross correlation functions between all pairs of the 248 sensors after prewhitening, i.e. converting the MEG time series to stationary, white noise series. This is achieved by modeling the raw series using AutoRegressive Integrative Moving Average (ARIMA) analysis, and taking the residuals. The CCF is then calculated for all possible pairs of these "prewhitened" series. These CCFs can be regarded as connectivity weights in a massively interconnected neural network, where the 248 sensors serve as nodes. Synchronous dynamic networks are constructed using the partial correlations derived from the zero-lag CCFs. An example of positive and negative interactions is shown in FIG. 2.

Figure 2B:
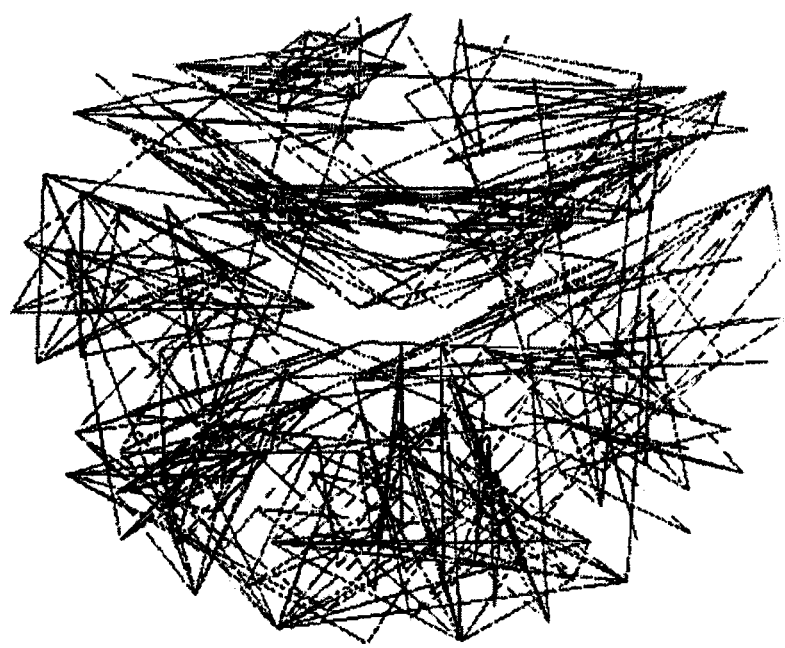

In FIGS. 2A and 2B, lines denote thresholded partial correlations (Fisher z-transformed). FIG. 2A illustrates positive partial correlations while and FIG. 2B illustrates negative partial correlations. There are 30,628 lines drawn (i.e. all possible pairs of 248 sensors) but only those exceeding the threshold below are depicted. The statistical significance threshold was adjusted to account for 30628 multiple comparisons according to the Bonferroni inequality: the nominal significance threshold is $p<0.001$, corresponding to an actual threshold used of $p<0.001/30628$ ($=p<0.00000003$). Analysis was based on a 45-s long time period without averaging or smoothing.

Discriminant Classification Analysis

Analysis is conducted to derive discriminant classification functions for certain groups of subjects with respect to selected measurements and then apply them to new cases to classify them in one of the original groups. This analysis yields posterior probabilities for classification to each group as well as a specific measure (squared Mahalanobis distance) which is the distance of the particular case from each of the classifying groups. This measure can serve to monitor potential changes in brain function to approximate that of different groups.

For example, consider AD. Data from subjects diagnosed with the disease (AD group) and subjects who are matched healthy controls (C) are used to derive two linear discriminant classification functions from the SNI data, one for AD and the other for C. A new subject with a potential initial diagnosis of mild cognitive impairment (MCI) is subjected to a SNI test. By applying the AD and C classification functions, an estimate is made as to what extent the new subject is healthy or AD. This assessment is not binary but rather continuous, as measured by the squared Mahalanobis distances to the centers of the AD and C groups in the canonical discriminant functions plot. These relative distances can serve as monitors of disease progression (subject will become more "AD-like"), regression (more "C-like"), or effect of intervention (→more "C-like" after drug treatment). Proximity refers to the relative distance and need not be displayed in graphical form in order to have meaning. Linear discriminant classification analysis can be used on a variety of conditions or diseases, including but not limited to, for example, AD, C and MCI data, as well as subjects with Sjögren's syndrome. A trend can be detected by monitoring over a period of time.

Human Subjects

In one example, subjects include those having various medical histories, in the age range of 13-90 years of age, include both male and female and all racial and ethnic groups. The present subject matter can be used with healthy subjects and subjects with disease affecting the nervous system including, multiple sclerosis (MS), Sjögren's syndrome (SS) or other autoimmune disorders with possible central nervous system involvement, MCI, AD, schizophrenia and chronic alcoholism. Embodiments of the present invention can be used with subjects having a variety of brain conditions. For example, a person under the influence of alcohol or a drug, Data Acquisition In one example, MEG data is acquired using a 248-channel axial gradiometer system (Magnes 3600 WH, 4D-Neuroimaging, San Diego, Calif.). The cryogenic helmet-shaped dewar of the MEG is located within an electromagnetically shielded room to reduce noise. Data (0.1-400 Hz) is collected at 1017.25 Hz. To insure against subject motion, five signal coils are digitized prior to MEG acquisition and consecutively activated before and after data acquisition, thereby locating the head in relation to the sensors. The MEG data includes a time series consisting of ~60,000 values per subject and sensor. Eye-related artifacts can be excluded by repeating the data collection.

Data Analysis

Data preprocessing includes removal of the cardiac artifact using the synchronous event-subtraction method. After removal of removal of the cardiac artifact, the time series is "prewhitened" so that interactions between them can be estimated without bias stemming from autocorrelations in the series themselves. Prewhitening is performed using Box-Jenkins ARIMA modeling to identify the temporal structure of the data time series using 25 lags, corresponding to ±25 ms. This analyses is conducted on ~60,000 time points. After ARIMA modeling and diagnostic checking, including computation and evaluation of the autocorrelation function (ACF) and partial ACF (PACF) of the residuals, an ARIMA model of 25 AR orders, 1st order differencing, and 1st order MA is applied to yield residuals stationary with respect to the mean, variance, and autocorrelation structure. Residuals are estimated using the SPSS statistical package (SPSS for Windows, Chicago, Ill., 2000). The zero-lag cross correlation between pairs of stationary residuals is computed using the DCCF routine of the IMSL statistical library (Compaq Visual Fortran Professional edition version 6.6B). From these, the partial zero-lag cross correlation between i and j sensors and its statistical significance is computed for all sensor pairs. In order to perform the linear discriminant analysis, this cross correlation is z-transformed to normalize its distribution: $z=0.5\,[\ln(1+r)-\ln(1-r)]$.

The linear discriminant classification analysis is performed using the DDSCRM subroutine of the IMSL Visual Fortran. The analysis is conducted using the cross-validated, leave-one-out method, and classification functions for each group is obtained using the reclassification method. For classification of individual cases, the discriminant scores, posterior probabilities, and squared Mahalanobis distances from each group centroid is calculated.

One aspect is to identify those sensor pairs which would classify cases correctly to their respective groups with zero uncertainly, i.e. with posterior probability of 1.0 for the correct group and 0.0 for all the other groups. The total set of available cross correlations is N=30,628 (=all possible pairs between 248 sensors). Given a predictor set size of, for example, k=7, the number of all possible permutations of k=7 out of $$N = 30,628, \frac{N!}{k!(N-k)!},$$

is astronomical. Hence the need of some special algorithm to efficiently search this immense space and identify sets of k=7 with the property to classify the subjects into the specific groups. In one example, a genetic algorithm is used.

Figure 3:
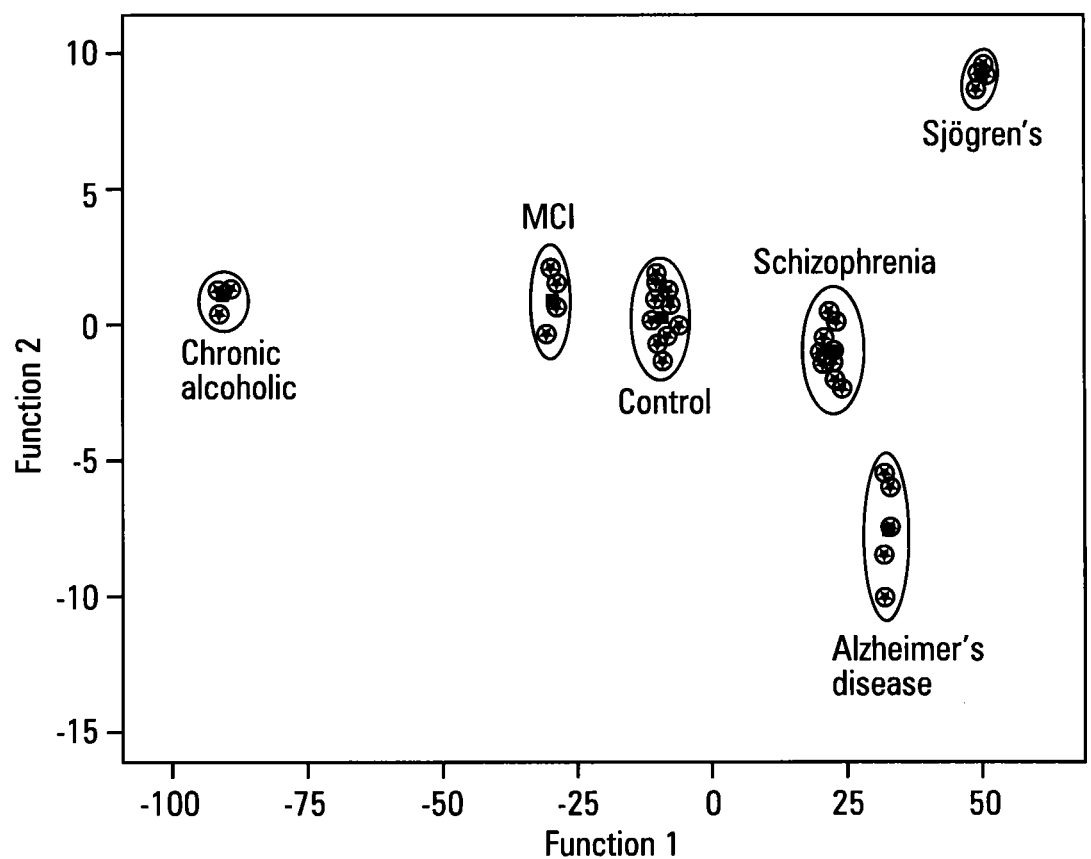
FIG. 3 illustrates an exemplary classification plot produced utilizing canonical discriminant functions.
Figure 4A:
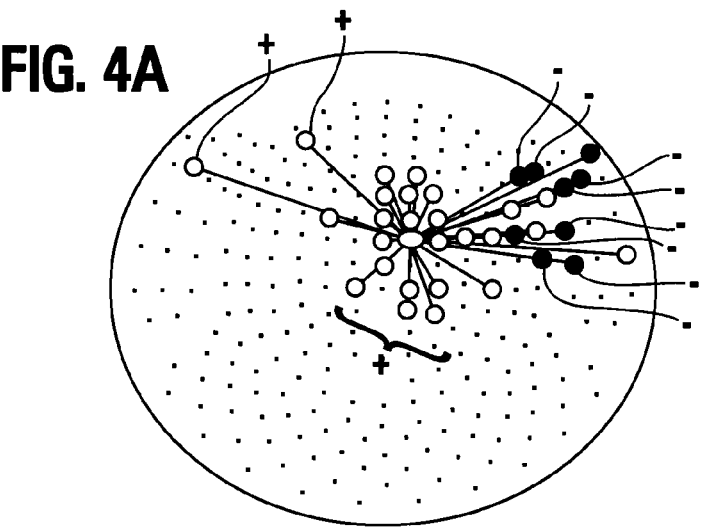
FIGS. 4A-4C illustrate spatial patterns for three separate sensors.
Figure 4B:
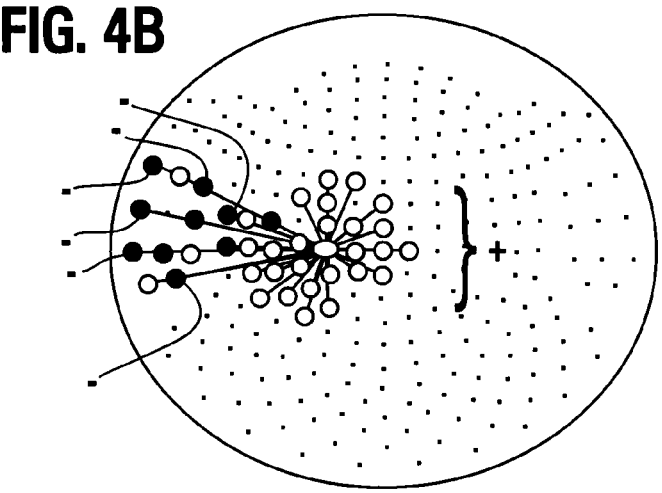
Figure 4C:
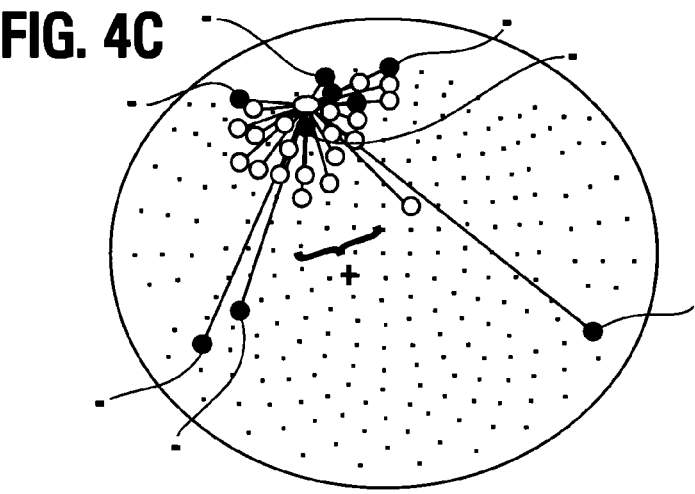
Figure 5A:
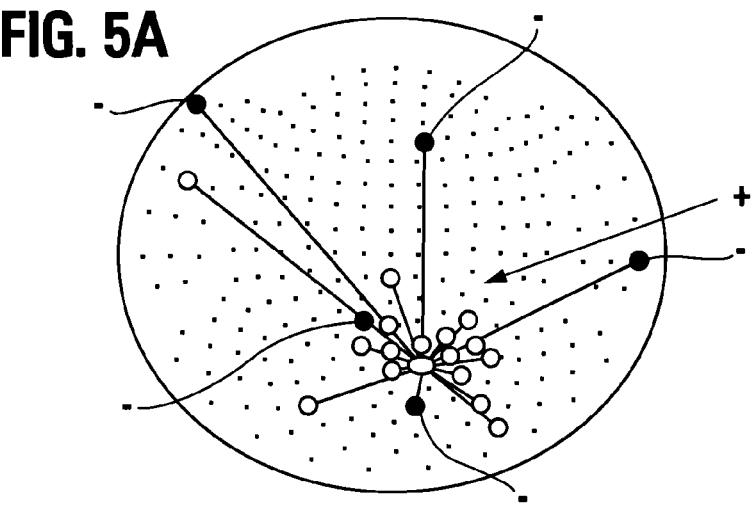
FIGS. 5A-5C illustrate spatial patterns for three more sensors.
Figure 5B:
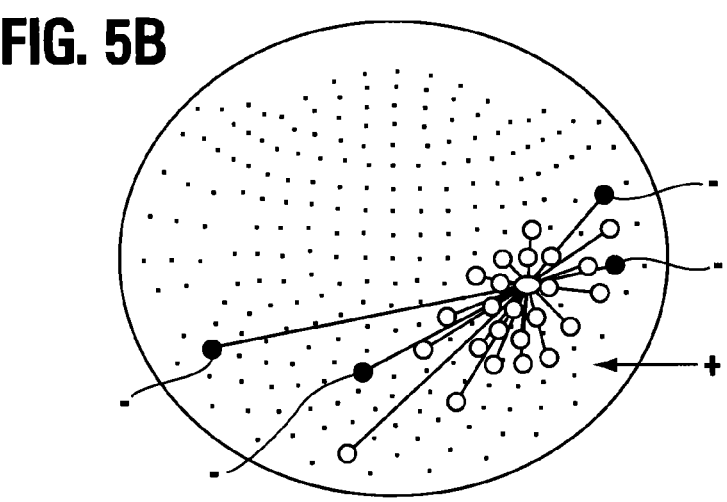
Figure 5C:
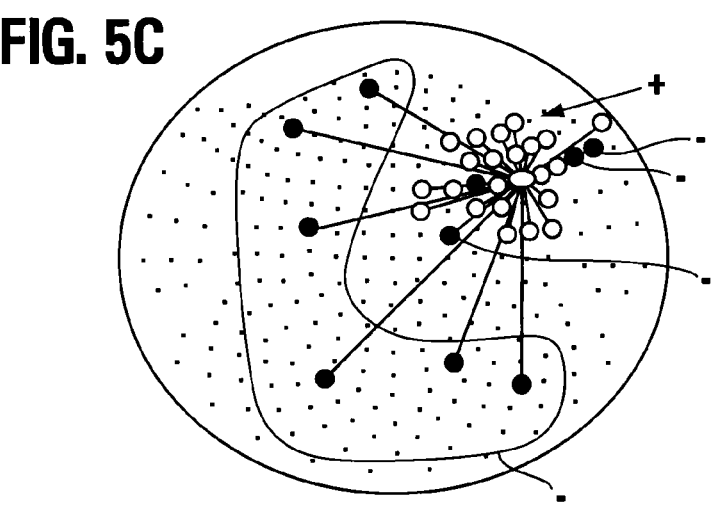

The plot shown in FIG. 3 illustrates results of the linear discriminant classification analysis of the zero-lag partial cross correlations. FIG. 3 illustrates classification plots for 50 using 40 cross correlations selected using a genetic search algorithm. The group centroids are distinguished by tight clustering and clear separation.

Example 3

Synchronous dynamic brain networks are visualized by using prewhitened (stationary) magnetoencephalography signals. In one example, data is acquired from 248 axial gradiometers. After fitting an autoregressive integrative moving average model, and taking the residuals, all pairwise, zero-lag, partial cross correlations $PCC_{IJ}^O$ between the i and j sensors were calculated, providing estimates of the strength and sign (positive and negative) of direct synchronous coupling between neuronal populations at a 1-ms temporal resolution. In one example, 51.4% of $PCC_{IJ}^O$ were positive, and 48.6% were negative. Positive $PCC_{IJ}^O$ occurred more frequently at shorter intersensor distances and were 72% stronger than negative ones, on the average. On the basis of the estimated $PCC_{IJ}^O$ dynamic neural networks are constructed (one per subject) showing distinct features, including several local interactions. These features were robust across subjects and can serve as a blueprint for evaluating dynamic brain function.

One use of whole-head magnetoencephalography (MEG) has been to localize sources of neural activity. Because this problem does not have a unique solution, the results of such analyses vary, depending on assumptions (single vs. multiple sources), realistic measurements (shape of the skull, "forward modeling"), specific methods of analysis, and subjective judgment. In addition, data typically are filtered down to ≈45 Hz and below, and analyses are performed based on the averages of many trials. Although the localization of activation by using MEG can be useful, other functional neuroimaging methods provide less equivocal information (i.e., information that does not depend on assumptions, etc.). These methods include fMRI and PET. With respect to the temporal resolution and time course of changes in brain activity, MEG and EEG have the edge. In such studies, data from single sensors are processed, typically many trials are averaged and aligned on a specific event of interest, and the shape of the time course is examined. The resulting MEG trace (or the event-related potential in EEG studies) provides valuable information on the timing of brain events with respect to behavior. A similar approach in fMRI, the event-related design, although useful, lacks the temporal precision of MEG and EEG signals.

According to embodiments of the present invention, whole-head, high-density MEG data is used to investigate the interactions among neural populations. Neural interactions underlie all brain functions, from sleep and wakefulness to higher cognitive processes. Evaluating the strength and spatial patterns of these interactions can contribute substantially to understanding of brain function and its relationship to behavior.

Methodology

Ten right-handed human subjects (five women and five men) participated in one experiment (age range, 25-45 years; mean±SEM, 33±2 years).

Stimuli are generated by a computer and presented to the subjects using a liquid crystal display projector. Subjects fixate on a blue spot of light in the center of a black screen for 45 s. The fixation point is presented by using a periscopic mirror system, which places the image on a screen=62 cm in front of the subject's eyes. MEG data was collected by using a 248-channel axial gradiometer system (Magnes 3600 WH; 4D-Neuroimaging, San Diego). The cryogenic helmet-shaped Dewar of the MEG is located within an electromagnetically shielded room to reduce noise. Data (0.1-400 Hz) is collected at 1017.25 Hz. To ensure against subject motion, five signal coils are digitized before MEG acquisition and consecutively activated before and after data acquisition, thereby locating the head in relation to the sensors. Pairwise distances between sensors is calculated as geodesics on the surface of the MEG helmet. Eye movements are recorded by using electrooculography. For that purpose, three electrodes are placed at locations around the right eye of each subject. The electrooculogram signal is sampled at 1017.25 Hz. The acquired MEG data included time series of ≈45,000 values per subject and sensor.

In one example, the interactions between time series in pairs of sensors is analyzed. For that purpose, individual series need to be stationary, i.e., "prewhitened"; otherwise, nonstationarities in the series themselves can lead to erroneous associations. Therefore, analyses included modeling the time series and deriving stationary (or quasistationary) residuals from which to compute pairwise association measures, such as cross correlations. Analyses described below is performed on single-trial, unsmoothed, and unaveraged data. A Box-Jenkins autoregressive integrative moving average (ARIMA) modeling analysis is performed to identify the temporal structure of the data time series by using 25 lags, corresponding to ±25 ms. This analyses is carried out on 45,676 time points. After extensive ARIMA modeling and diagnostic checking, including computation and evaluation of the autocorrelation function and partial autocorrelation function of the residuals, it was determined that an ARIMA model of 25 autoregressive orders (equal to the ±25-ms lags), first-order differencing, and first-order moving average is adequate to yield residuals that were practically stationary with respect to the mean, variance, and autocorrelation structure. Residuals were estimated by using the SPSS Version 10.1.0 statistical package for WINDOWS (SPSS, Chicago). The zero-lag cross correlation between pairs of stationary residuals was computed by using the DCCF routine of the International Mathematics and Statistical Library (COMPAQ VISUAL FORTRAN PROFESSIONAL EDITION Version 6.6B, Compaq, Houston). From these data, the partial zero-lag cross correlation $PCC_{IJ}^O$ between the i and j sensors and its statistical significance were computed for all sensors. To calculate descriptive and other statistics, $PCC_{IJ}^O$ is transformed to $Z_{IJ}^O$ by using Fisher's z-transformation to normalize its distribution:

$$Z_{IJ}^O = 0.5[\ln(1+PCC_{IJ}^O)\ln(1-PCC_{IJ}^O)].$$

Exemplary results are as follows: Given 248 sensors, a total of 248!/2!246!=30,628 $PCC_{IJ}^O$ are possible per subject for a grand total of 30,628×10 subjects=306,280 $PCC_{IJ}^O$. Of those correlations, 285,502 (93.2%) were analyzed after excluding records with eye blink artifacts; 81,835/285,502 (28.7%) of those correlations were statistically significant (P<0.05). Of all valid $PCC_{IJ}{}^O$, 146,741 (51.4%) were positive and 138,761 (48.6%) were negative. The average (+SEM) positive $Z_{IJ}{}^O$ was 0.0112±0.00004 (maximum $Z_{IJ}{}^O$=0.38; $PCC_{IJ}{}^O$=0.36); the average negative $Z_{IJ}{}^O$ was −0.0065±0.00002 (minimum $Z_{IJ}{}^O$=$PCC_{IJ}{}^O$=−0.19). The absolute values of these means differed significantly (P<$10^{-20}$; Student's t test), the average |+$Z_{IJ}{}^O$| being 72% higher than the average |−$Z_{IJ}{}^O$|. Examples of spatial patterns in the distribution of synchronous coupling between a sensor and all other sensors are illustrated in FIGS. 4A-4C and 5A-5C. Only statistically significant $PCC_{ij}{}^o$ are plotted. The statistical significance threshold was adjusted to account for 247 multiple comparisons per plot, according to the Bonferroni inequality: the nominal significance threshold is P<0.05, corresponding to an actual threshold used of P<0.05/247 (i.e., P<0.0002). Positive and negative $PCC_{ij}{}^o$ are indicated. small dots represent the location of the 248 sensors, projected on a plane. Data are from one subject.

Relation Between $PCC_{ij}{}^o$ and Intersensor Distance.

Overall, $PCC_{IJ}{}^O$ varied with the distance, $\bar{d}_{ij}$, between sensors i and j. In general, sensors closer to each other tended to have positive $PCC_{IJ}{}^O$. The average intersensor distance $\bar{d}_{ij}$ for negative $z_{ij}{}^o$ was 24% longer than for positive $z_{ij}{}^o$. Specifically, $\bar{d}_{ij}$ (−$z_{ij}{}^o$) was 198.92±0.21 mm (n=138,700), and $\bar{d}_{ij}$ (−$z_{ij}{}^o$) was 160.12±0.24 mm (n=146,675). Overall, there was a strong and highly significant negative association between $z_{ij}{}^o$ and the log-transformed $d_{ij}$, $\ln(d_{ij})$. The Pearson correlation coefficient between signed $z_{ij}{}^o$, and $\ln(d_{ij})$ was −0.519 (P<$10^{-20}$). This relation indicates that the strength of synchronous coupling tended to fall off sharply with intersensor distance.

Synchronous Dynamic Neural Networks.

Figure 7:
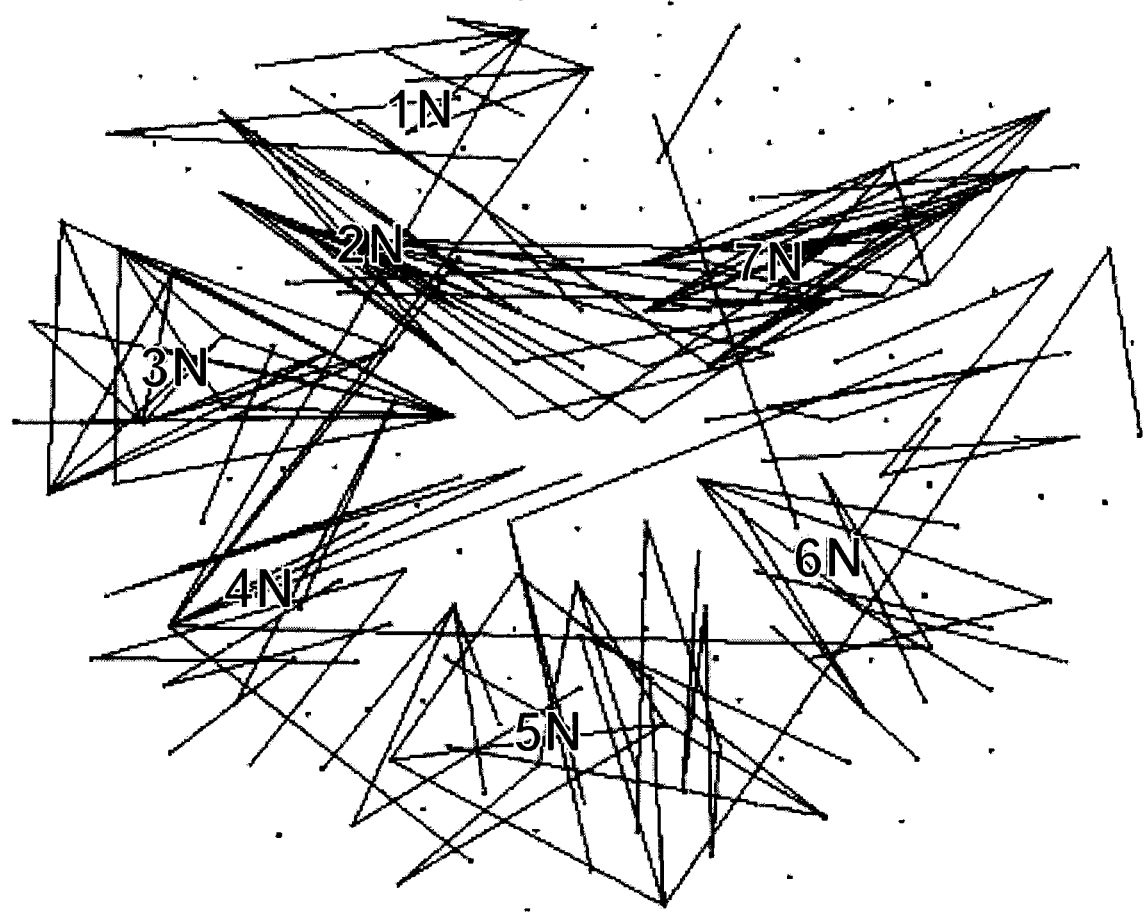
Figure 8A:
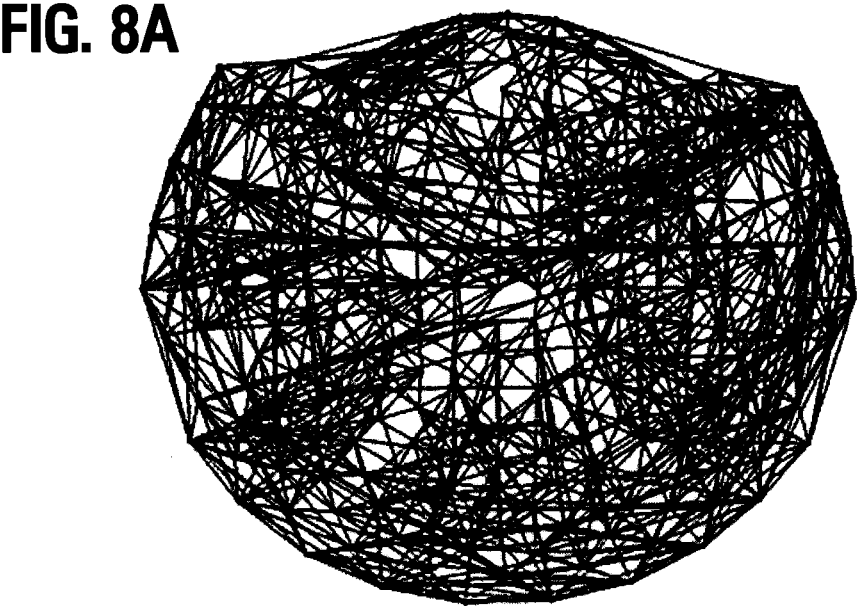
Figure 8B:
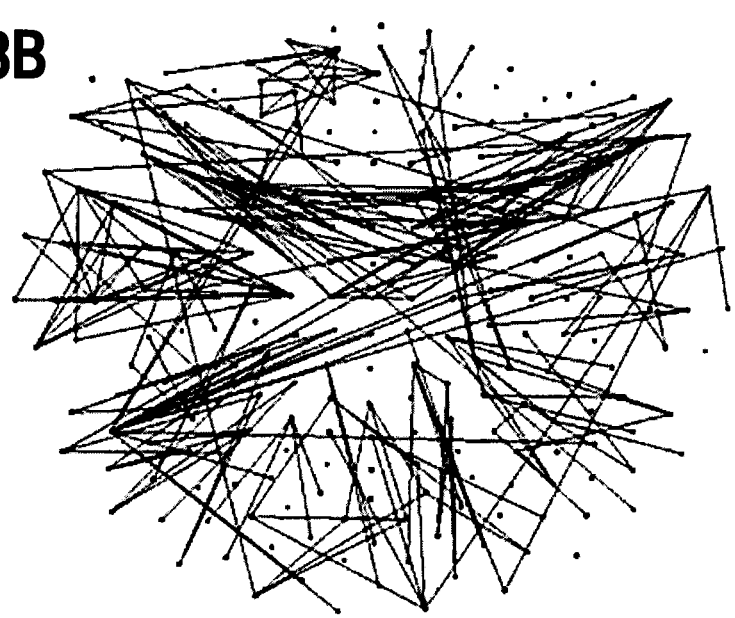
Figure 9A:
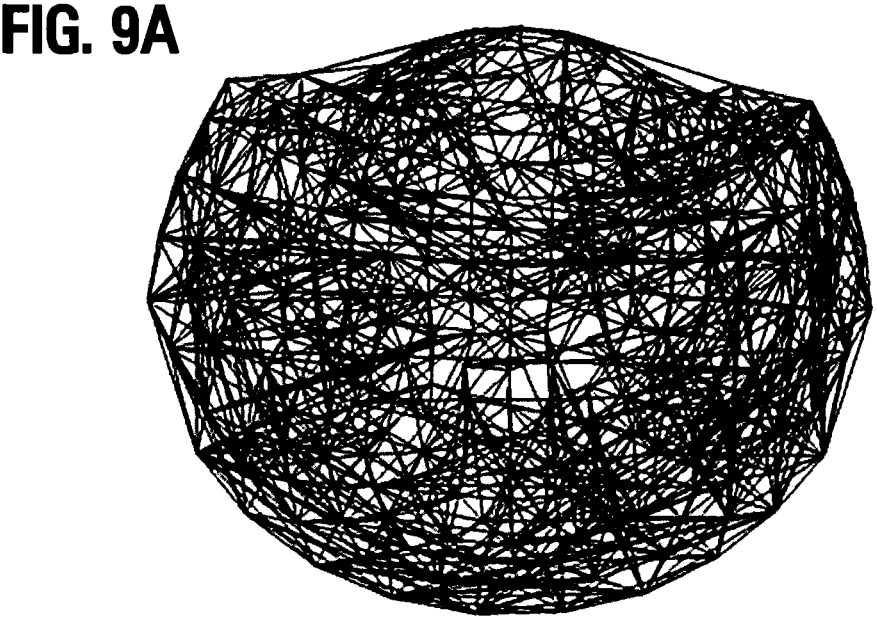
Figure 9B:
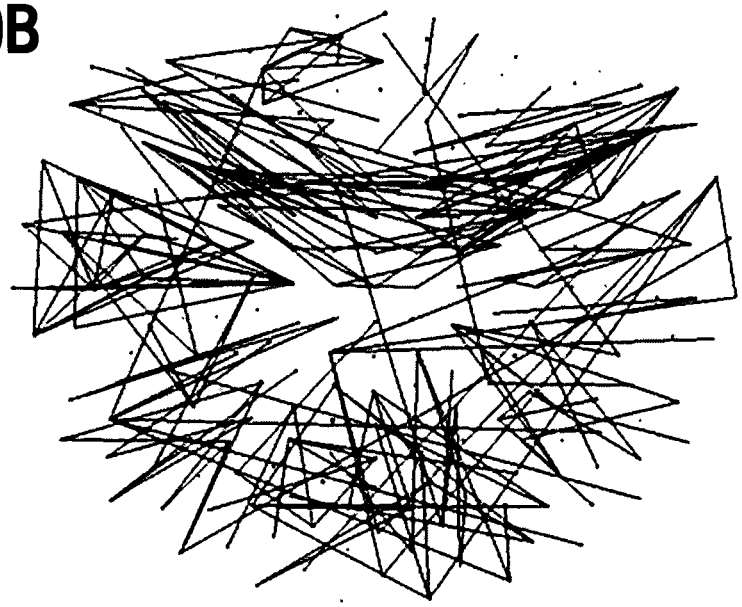

The $PCC_{ij}{}^O$ is an estimate of synchronous coupling between neuronal populations in which the absolute value and $PCC_{IJ}{}^O$ denote the strength and kind of coupling, respectively. If the neural ensembles sampled by the 248 sensors are considered nodes in a massively interconnected neural network, such as the massively connected neural network map visualized in FIGS. 6-7, then the $PCC_{IJ}{}^O$ can serve as an estimate of the dynamic synchronous interactions between these nodes. Such a massively interconnected network can be visualized by connecting the 248 nodes with lines and indicating whether each line represents a positive or a negative coupling. FIGS. 6 and 7 show a thresholded and scaled view of this network, averaged across the 10 subjects; regional variations in interactions were present and consistent across subjects.

Features noted in this network include: (i) most of the next-neighbor interactions are positive; (ii) most of negative interactions occur at longer distances; (iii) interactions with centrally located sensors are relatively sparse; and (iv) inter-hemispheric interactions are infrequent, probably because of the longer distances involved. In addition, systematic variations in the local density of interactions can be distinguished qualitatively, as follows (in counterclockwise direction). There were nine regions of positive interactions (FIG. 6), consisting of sensors overlying the following brain regions: left anterior-frontal (1P), left dorsal-frontal (2P), left lateral-frontal-temporal (3P), left parietal (4P), left parietal-occipital (5P), right occipital (6P), right parietal-temporal (7P), right temporal (8P), and right frontal (9P). For negative interactions (FIG. 7), seven regions could be distinguished, consisting of sensors overlying the following brain regions: left anterior-frontal cortex (IN), left dorsal-frontal (2N), left lateral-frontal-temporal (3N), left parietal (4N), occipital (5N), right parietal (6N), and right frontal (7N). Several of the positive and negative interactions were spatially overlapping.

Robustness of Network Across Subjects

Remarkably, neural networks constructed as above were very similar across subjects (FIGS. 8A and 8B, and 9A and 9B). Overall network similarity can be quantified and assessed between all subject pairs by calculating the Pearson correlation coefficient across all $z_{ij}{}^o$ (i.e., all i and j sensors) of the network. The correlation coefficients obtained are high and highly significant (median=0.742; range, 0.663-0.839; P<10-20 for all correlations; >20,000 degrees of freedom). These findings suggest a common network foundation.

This example embodiment assesses synchronous dynamic coupling between single-trial MEG time series made stationary by using ARIMA modeling. The results obtained are estimates of this coupling, uncontaminated by nonstationarities typically present in raw MEG data. Zero-lag cross correlations are used to estimate synchronous coupling between two time series. From these correlations, partial correlations are computed, which provides an estimate of sign and strength of direct coupling between two sensor series because possible effects mediated indirectly by other sensors are removed. In addition, the $PCC_{IJ}{}^O$ allowed construction of a synchronous dynamic network in which the sign and strength of the $PCC_{IJ}{}^O$ serve as estimates of the sign and strength of direct neuronal population coupling. In general, $PCC_{IJ}{}^O$ are smaller than the raw cross correlations because all other possible 246 associations in the sensor ensemble are accounted for. However, small-amplitude interactions are the rule for stability in massively interconnected networks. For example, in a previous study of such networks, the normalized connection strength ranged from −0.5 to 0.5 at the beginning of training of the networks but ranged from approximately −0.2 to 0.2 in the trained, stable network. Comparably, using the present subject matter, the range of $PCC_{IJ}{}^O$ as similar (−0.19 to 0.36). $PCC_{IJ}{}^O$ are positive or negative and of various strengths depending on the particular pair of sensors and their distance, such that $PCC_{IJ}{}^O$ tend to be higher at short distances. This tendency may be due to multiple detectors viewing the same neural sources. Although there is no quantitative measure of this component, the results assure that it does not dominate the correlation patterns seen. Specifically, the rapid fall of the magnetic field strength with distance, along with the effect of gradiometer coils, would result in a very tight pattern of correlations of signal due to this contribution, with no distant interactions visible on the same scale. However, the analysis reveals complex patterns of interactions over the entire cortex, visible on a single amplitude scale. The correlations shown are stronger for near sensors, but neural activity is generally more correlated locally. The calculation of partial correlations serve to eliminate potentially spurious effects.

In previous studies, associations between neuronal ensembles (recorded as EEG, MEG, or local field potentials) have been investigated by using frequency-domain or time-domain analyses applied to a whole data set or within specific spectral frequency bands. In such analyses, association measures are commonly calculated from the data without testing for their stationarity. Stationarity (or quasistationarity) provides accurate measurements of moment-to-moment interactions between time series (as contrasted to shared trends and/or cycles), both in the time domain (by computing cross correlation) and in the frequency domain (by computing squared coherency). Cross correlation or coherency estimates based on raw nonstationary data yield erroneous estimates and spurious associations.

The sign of cross correlation does not provide information regarding underlying excitatory or inhibitory synaptic mechanisms but merely indicates the kind of simultaneous covariation with respect to the mean of the series: a positive correlation indicates covariation in the same direction (increase/increase, decrease/decrease), whereas a negative correlation indicates covariation in opposite directions (increase/decrease, decrease/increase). In general, $PCC_{IJ}^{O}$ tend to vary in an orderly fashion in sensor space, such that it tends to be positive between neighboring sensors and negative between sensors farther away. Although this tendency was noted, there are clear and distinct exceptions, including negative $PCC_{IJ}^{O}$ between neighboring sensors and positive $PCC_{IJ}^{O}$ between far-away sensors. In addition, the spatial $PCC_{IJ}^{O}$ pattern differed depending on the location of the reference sensor. The findings suggest a robust and relationally orderly correlation structure, but with distinct local specificity. Indeed, these characteristics are the fundamental attributes that endow the resulting massively interconnected network with the characteristic structure illustrated in FIGS. 6-9B.

One feature of this structure was the partitioning of the overall network into regional variations in the strength of positive or negative interactions. The delineation of these mixed interactions is another step in this approach, together with an attempt to localize the interactions in brain space by using, e.g., current-density or beam-forming techniques.

Cardiac Artifact Removal Algorithm

Cardiac artifacts can be removed using various procedures, including, for example, the following:

A representative heartbeat is selected to be used as a starting template. In one example, a previously saved template from a different subject is used. The representative template is then conjugated (or slid through the data), one point at a time, with the correlation of the template with the overlapping data segment calculated at each step. The resulting correlation time course is used to determine the locations of the heartbeats. When the correlation exceeds a threshold, a heartbeat is recorded at the local maximum in the correlation time course.

To reduce the possibility of false detections due to noise, minimum and maximum heart rates are selected to create a time window, relative to the preceding beat, in which each beat is expected. Peaks in the correlation before the start of the window are ignored, and the beat is taken at the highest peak in correlation during the window, rather than the first one that meets threshold. If no peak within the window meets threshold, then a missed beat is assumed and the window is expanded until it includes a peak that meets the threshold. Both the time window and the correlation threshold are adjusted for each subject to maximize true detections and minimize false detections.

If detection is imperfect, then an improved template is created by averaging the beats that were actually detected, and a second correlation calculation is made with the improved template. Detection is generally complete enough with the second pass that additional passes are not beneficial in improving the template. After the second pass, heart-rate tracings with a range of correlation thresholds are viewed and the one highest threshold that achieves complete (or near complete detection), without significant numbers of false detections, is kept. These detections are then used to create a final averaged cardiac waveform. A one-second segment of data is taken around the detection to include the whole of the heartbeat. Beats with high noise are not included in the average, and the waveform is DC shifted to be zero average value before and after the extended heartbeat. The averaged waveform for each channel is thus created using only signal from that channel. The averaged waveforms are then subtracted from the channels at each detected occurrence of the heartbeat. If the heart rate is high, then the tail of the waveform is cut to just before the start of the next beat. The result is a cardiac artifact removal that does not introduce false correlations between channels.

If a single data file is less than a few minutes, the averaged waveform used for subtraction is made cleaner by taking a weighted average of multiple averaged waveforms from the same recording session.

Prewhitening of MEG Time Series

Relations between time series can be assessed if the series are essentially stationary, i.e. the mean and variance do not differ for different time points in the series and the autocorrelation (ACF) and partial autocorrelation functions (PACF) are flat. If these conditions are not fulfilled, then erroneous results are obtained stemming from the influence on a given value X at time t of previous values of X, the possible presence of trends, and the carry over of noise from previous values onto the current value.

In one example of the present subject matter, the data is processed by prewhitening. Prewhitening refers to the removal of such dependencies as described above. Prewhitening can, but need not, also entail assuring that these dependencies have been effectively removed.

In one example, prewhitening includes modeling the time series using autoregressive, integrative and moving average components, and taking the residuals.

Since practically every time series is unique, the modeling of a time series can be a tedious, complicated and iterative process involving (a) identifying the important components of the model, (b) estimating the modeling coefficients and their stability, (c) taking the residuals, and (d) assessing the stationarity of the residuals.

The identification of the time series model is done by inspecting the shape of the ACF and PACF. The estimation of the modeling coefficients can be done in different ways, especially those involving the moving average component. The estimation of the residuals is straightforward, as is their assessment using ACF and PACF. If the residuals are not adequately stationary, then the process is repeated by changing the model parameters, etc., until stationarity is achieved.

Since this modeling involves (a) combinations of factors (autoregression, differencing, moving average) and (b) several potential levels within each factor (e.g. number of autoregressive orders, number of differencing, and number of orders of moving average), and since an individual time series of the length considered here (~60,000 time points) is essentially unique, there is no single rule to achieve the goal of stationarity.

For that purpose, a number of different computations can be used to find that combination which satisfies the stationarity requirements. As with the removal of the cardiac artifact, an element of judgment is involved in simultaneously evaluating the results obtained. While the mathematical description of the elementary operations (e.g. differencing, etc.) are straightforward, determining a suitable combination can be tedious.

Several platforms may be used in this process, including FORTRAN, MATLAB, SPSS statistical package and BMDP statistical package. The actual employment of specific platforms depends on the specific series. Regardless of the particular combination selected, the objective is to achieve adequate stationarity.

Example 4

This example demonstrates the power of subsets of partial zero-lag neural correlations to discriminate and correctly classify subjects into to six different groups of neurophysiologic conditions.

Methods

Fifty-two human subjects participated in a study as paid volunteers. There were 6 groups, including healthy controls, and subjects with Alzheimer's disease, schizophrenia, multiple sclerosis, Sjögren's syndrome, and chronic alcoholism. The composition of each group was as follows: Alzheimer's disease (N=6 men, age 76.8±1.8 y, mean±SEM); schizophrenia (N=9 [7 men, 2 women], age 48.2±2.9 y); multiple sclerosis (N=4 [2 men, 2 women], age 42.5±6.4 y); Sjögren's syndrome (N=4 women, age 56.3±5.2 y); chronic alcoholism (N=3 men, age 57±0.9 y); healthy (control) (N=25 [17 men and 8 women], age 47.0±3.6, range: 23-82 y).

Subjects belonging to a subject group had a functional brain disorder, and their diagnoses were made by a specialist in the respective field of medicine. The subjects with chronic alcoholism had not taken alcohol for 24 h preceding the study and had tested alcohol-free using breath-analyzer. The control group comprised age-matched subjects to the subject groups, as well as other healthy subjects. All subjects, except for those belonging to the control group, were receiving medications relevant to their brain illness; some of these medications were psychotropic.

Data Acquisition

Subjects lay supine in the MEG instrument and fixated their eyes on a spot, ~62 cm in front of them, for 45-60 s (in different subjects) while MEG data were acquired from 248 axial gradiometers (0.1-400 Hz, sampled @ 1017 Hz; Magnes 3600 WH, 4-D Neuroimaging, San Diego, Calif.). This yielded, for each subject, a data set consisting of 248 time series with 45000-60000 time points. The cardiac artifact was removed from each series using event-synchronous subtraction as described above.

Data Analysis

All analyses described below were performed on single-trial, unsmoothed and unaveraged data. Following "prewhitening" of the time series using Box-Jenkins ARIMA modeling, the partial zero-lag cross-correlation $PCC_{ij}^o$ between i and j sensors (N=248 sensors) was computed for all sensor pairs (N=30628). $PCC_{ij}^o$ was transformed to $z_{ij}^o$ using Fisher's z-transformation to normalize its distribution:

$$z_{ij}^o = 0.5[\ln(1+PCC_{ij}^o) - \ln(1-PCC_{ij}^o)].$$

Next, a determination was made as to whether subsets of $z_{ij}^o$ exist that would correctly classify subjects into their respective groups. For that purpose, linear discriminant analysis was performed using the robust leave-one-out method, and requiring 100% correct classification of every subject to its corresponding group to accept a given subset of $z_{ij}^o$ as a good classifier.

A brute-force approach in identifying all such subsets would be possible, computationally burdensome. For example, for a subset of 5 predictors, the total number of possible combinations would be:

$$\frac{(30628!)}{(5!)(30623!)} = 224527811140901268000$$

For that reason, a genetic algorithm was used to reduce computational time and optimize the search. Using the genetic algorithm, an initial subset of a certain number of $z_{ij}^o$ predictors (out of the 30628 available) was chosen randomly, and a micro-GA of population size=5 and uniform crossover was let to run for 24 hours. If, during the search, the fitness function solution was constant for $2 \times 10^5$ generations, a new random subset was chosen and the operation repeated.

Results

Figure 10:
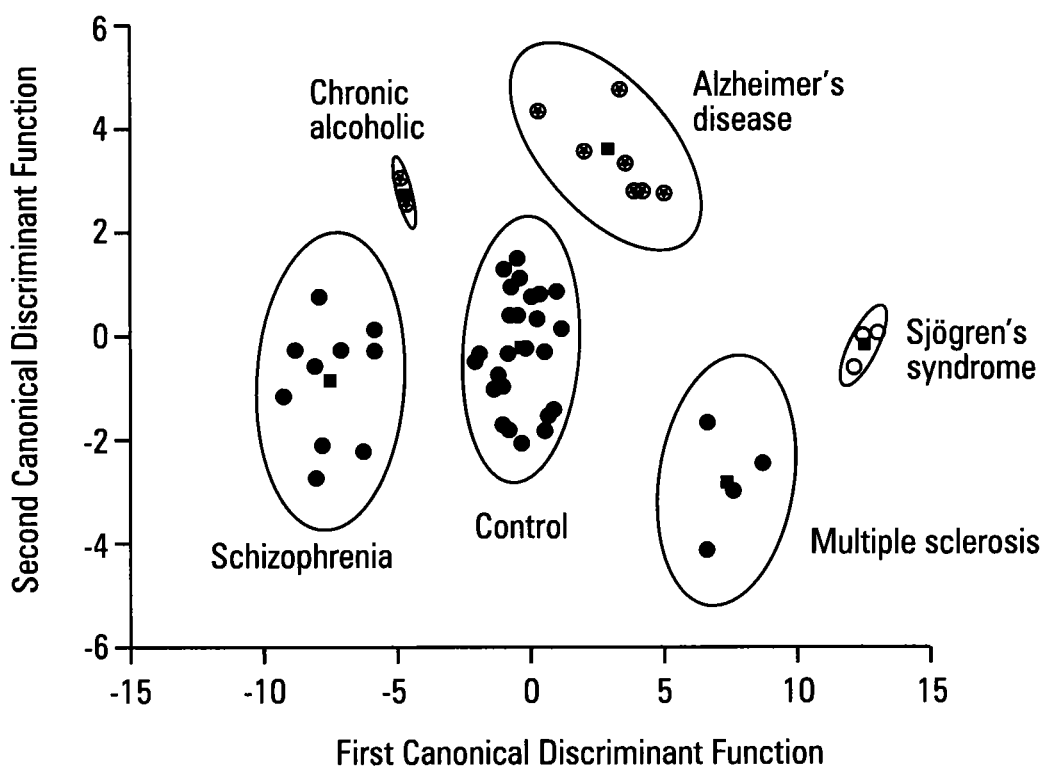
FIG. 10 illustrates another exemplary classification plot produced utilizing canonical discriminant functions.

Using the genetic search algorithm, subsets of $z_{ij}^o$ were readily found that classified each subject 100% correctly to the respective group. An example diagram of the classification (mapped to 2-d space) is illustrated in FIG. 10. All groups were clearly distinguished with no overlap in the canonical discriminant function (CDF) space of the first 2 CDFs.

A CDF is a weighted linear sum of the predictor variables and is derived by the statistical analysis. For L groups (assuming L is smaller than the number k of predictors in a subset), there are j=L−1 discriminant functions, $CDF_i$, where i=1, 2, ..., j. Given six groups in these data, there are always five CDFs for k>L. For a given subset of predictors, the statistical significance of CDFs i=1 through 5, 2 through 5, 3 through 5, etc. is assessed by Wilk's Λ test statistic. Wilk's Λ was highly significant for CDFs of i=1 through 5 (p<10-22), 2 through 5 (P<10−6), and 3 through 5 (P=0.004); it was not significant for CDFs of 4 through 5 (P=0.16), and CDF 5 (P=0.71). Subjects were classified 100% correctly in their respective groups. Finally, the null hypothesis of equality of the six group centroids in the original, raw-data 20-dimensional $z_{ij}^o$ predictor space was tested using a multivariate analysis of variance and was rejected at a high level of significance (P<10−31, Hotteling's Trace test).

Testing Against Chance

The number of qualifying subsets expected by chance depends on the number of actual predictors, k, in a subset, the ensemble size of all possible predictors $z_{ij}^o$, the number of groups, and the number of subjects to be classified. Given M subjects belonging to L groups, and subsets of the same size of k predictors out of N (=30628) possible, the expected number s of subsets that would give 100% correct classification of each subject to its group by chance is:

$$S = Q\left(\frac{1}{L}\right)^M, \quad Q = \frac{N!}{k!(N-k)!}$$

This formula assumes testing all possible subsets Q of size k, a practically impossible task for even small values of k, given the large value of N (=30628). Nevertheless, this problem was investigated in the following, tractable ways. The first analysis took advantage of the fact that an exhaustive search is feasible for small k, L and M. Such a search was carried out for k=2, N=30628, L=3, and M=17 (6 subjects with Alzheimer's disease, 3 subjects with chronic alcoholism, and 8 matched controls). This exhaustive assessment yielded 560 subsets with 100% correct classification of each subject, as compared to ~4 sets (s=3.63) expected by chance. These proportions (over Q=469021878 total possible subsets) differed significantly (binomial theorem, normal deviate z=23.4, P<10-50), indicating an excess (above chance) of good sets. Finally, the following analysis was performed for a larger set for which an exhaustive search would be infeasible. For k=10, N=30628, L=6, and all M=52 subjects, the expected number of subsets yielding 100% correct classification is essentially zero (s=0.0069). However, the discriminant classification program, using the genetic algorithm, yielded 79 sets with 100% correct classification after running for several hours. Although the exact proportion of good sets in the data cannot be calculated (since an exhaustive search is not feasible), this proportion already exceeds the chance expectation (z=8.78, P<10−50). In many cases, successful subsets yielded not only 100% correct classification but also high (e.g., >0.98) posterior probabilities of correct classification of each subject to its group.

Discussion

One aspect of the invention underlying the successful classification obtained in this example is the pairwise zero-lag partial cross correlation of MEG time series. The set of all such correlations among the signals for the 248 MEG sensors characterize dynamic synchronicities in a large neural network. The results suggest that these synchronicities might be regulated, since their alteration even within small subsets is a powerful discriminant of brain disease states. This idea is in accord with the observation that the brain pattern of partial correlations is very similar among healthy subjects and with the broader concept of synchronicity as a substrate for higher brain function.

Early pioneering work using quantitative EEG went a long way in laying the foundation for the application of discrimination and classification of electrophysiological brain patterns in health and disease. Conceptually, the approach of some embodiments of the present invention follows those early leads but factually it differs substantially, for (i) it utilizes more accurate measuring technology (MEG vs. EEG); (ii) it is based on a single trial (vs. averaged) trials; (iii) its basic tool is a relational measure between sensor signals (cross-correlation) instead of raw (e.g. signal amplitude) or derived (e.g. spectral power in particular frequency band) measures within individual sensors; and (iv) this cross-correlation is computed from stationary time series (after prewhitening of the raw neural signal) so that it reflects true moment-to-moment neural interactions. Additionally, (v) the strength of synchronicity is measured at high temporal resolution of about (1 ms); and (vi) interactions of a given pair is partialed-out with the rest of the neural network, so that the resulting partial zero-lag cross-correlations are not contaminated by collinearities.

Example 5

In this example, interactions of neural populations were tested as classifiers of brain status and their potential as biomarkers was evaluated for several brain diseases in a total of 142 subjects. For that purpose, initially, 52 subjects were studied to derive discriminant classification functions. These functions were subsequently applied to a new group of 46 subjects in an external cross-validation procedure. Finally, 44 additional subjects were most recently incorporated for a complete sample of 142 subjects. Synchronous neural interactions classified brain status successfully and gave excellent external validation results.

Materials and Methods

A total of 142 human subjects participated in a study as paid volunteers. There were 7 groups, including healthy controls (HC), patients with Alzheimer's disease (AD), schizophrenia (SZ), chronic alcoholism (CA), Sjögren's syndrome (SS), multiple sclerosis (MS) and facial pain (FP). The composition of each group was as follows. HC (N=89 [48 men, 41 women], age [mean±SEM] 43.7±1.7, range: 10-82 y); AD (N=9 men, age 74.0±2.1 y, average mini-mental state examination [MMSE] score 21.13±1.5); SZ (N=16 [13 men, 3 women], age 45.8±2.5 y); CA (N=3 men, age 57.3±0.9 y); SS (N=10 [1 man, 9 women], age 54.8±3.2 y); MS (N=12 [4 men, 8 women], age 40.7±3.3 y, secondary progressive or relapsing remitting forms); FP (N=3 women, age 47.3±6.5 y, arthromyalgia). Subjects belonging to a patient group had a functional brain disorder, and their diagnoses were made by a specialist in the respective field of medicine, as follows. AD patients were diagnosed based on an interdisciplinary consensus diagnosis conference and determined to meet criteria for (i) a diagnosis of dementia according to DSM-IV [7] and (ii) possible or probable AD according to NINCDS-ARDA criteria. SZ patients were diagnosed based on DSM-IV criteria, had no history of electroconvulsive therapy, no head trauma (overnight hospitalization or unconscious for >5 minutes), no past substance dependence, no current substance/alcohol dependence or abuse, and no medical conditions that effect the central nervous system (e.g. epilepsy). CA patients had not taken alcohol for 24 h preceding the study and had tested alcohol-free using breath-analyzer. SS patients were diagnosed based on the classification criteria by the American-European consensus group for Sjögren's syndrome. They complained of cognitive dysfunction verified clinically by their physicians and by neuropsychological measurements. MS patients met the modified McDonald criteria [10], had greater than or equal to 10 T2 cerebral lesions, were at least 30 days post relapse or steroid burst, and had a clear MS subtype. FP patients were diagnosed with temporomandibular joint arthralgia and myofascial pain of the masticatory muscle (arthromyalgia). Finally, the control group comprised age-matched subjects to the patient groups, as well as additional healthy subjects. All subjects, except for those belonging to the control group, were receiving medications relevant to their brain illness; some of these medications were psychotropic.

For purposes of external cross-validation, two consecutive sub-samples of subjects were analyzed based on an arbitrary time point unrelated to data analysis. The $1^{st}$ sample comprised 52 subjects (6 groups) and consisted of the following groups: HC (N=25 [17 men, 8 women], age 47.0±3.6, range: 23-82 y); AD (N=6 men, age 76.8±1.8 y); SZ (N=10 [7 men, 3 women], age 48.2±2.9 y); CA (N=3 men, age 57.3±0.9 y); SS (N=4 women, age 56.3±5.2 y); MS (N=4 [2 men, 2 women], age 42.5±6.4 y). The $2^{nd}$ sample comprised 46 subjects (5 groups) whose data were processed following the $1^{st}$ sample. This sample consisted of the following groups: HC (N=33 [15 men and 18 women], age 36.8±2.8, range: 11-67 y); AD (N=2 men, age 76.0±3.0 y [73, 79]); SZ (N=2 men, age 30.0±2.0 y [27, 33]); SS (N=5 [1 man, 4 women], age 51.4±4.5 y); MS (N=4 [2 men, 2 women], age 36.8±5.2 y).

Task—Data Acquisition

The goal here was to have the brain in a stable condition without engaging in any specific task. For that purpose, subjects lay supine in the MEG instrument and fixated their eyes on a spot, ~62 cm in front of them, for 45-60 s (in different subjects) while MEG data were acquired from 248 axial gradiometers (sampled @ 1017 Hz, filtered 0.1-400 Hz; Magnes 3600 WH, 4-D Neuroimaging, San Diego, Calif.). This yielded, for each subject, a data set consisting of 248 time series with 45,000-60,000 time points. The cardiac artifact was removed from each series using event-synchronous subtraction.

General Data Analysis

All analyses described below were performed on single-trial, unsmoothed and unaveraged data. To compute the zero-lag cross correlation between MEG sensor time series, individual series were made stationary by "prewhitening," for nonstationarities in the series can lead to erroneous associations. Therefore, the first step in the analyses was to model the time series and derive stationary (or quasi-stationary) residuals from which to compute pairwise association measures, such as cross-correlations. Previous work showed that an ARIMA model of 25 AR orders, $1^{st}$ order differencing, and $1^{st}$ order MA was adequate to yield residuals that were practically stationary with respect to the mean, variance, and autocorrelation structure. Residuals were estimated using the SPSS statistical package (SPSS for Windows, version 15, SPSS Inc., Chicago, Ill., 2006). The zero-lag cross-correlation between pairs of stationary residuals was computed using the DCCF routine of the IMSL statistical library (Compaq Visual Fortran Professional edition version 6.6B). From these, the partial zero-lag cross-correlation $PC_{ij}^O$ between i and j sensors and its statistical significance were computed for all sensor. In order to calculate descriptive and other statistics, $PCC_{ij}^O$ was transformed to $z_{ij}^O$ using Fisher's z-transformation to normalize its distribution:

$$z_{ij}^O = 0.5[\ln(1+PCC_{ij}^O) - \ln(1 PCC_{ij}^O)]$$

Univariate analyses of covariance (ANCOVAs) were performed on the data of each individual sensor pair for each sample, where $z_{ij}^O$ was the dependent variable and the gender (binary variable) and age were covariates. To assess the congruence of the distribution of the Group effect among sensor pairs in the $1^{st}$ and $2^{nd}$ sample, the presence or absence of a significant effect for a given sensor pair as 1 and 0, respectively were coded, and the $\chi^2$ test statistic was computed.

Linear Discriminant Classification Analysis

This analysis was used to determine whether subsets of $z_{ij}^O$ exist that would correctly classify subjects into their respective groups. In this analysis, Fisher's group discrimination and subject classification are done in a canonical discriminant function (CDF) space. CDF is a weighted linear sum of the predictor variables and is derived by the statistical analysis. For L groups (assuming L is smaller than the number k of predictors in a subset), there are j=L−1 discriminant functions, $CDF_i$, where i=1, 2, ..., j. Group discrimination (and individual subject classification) is performed within this multidimensional CDF space. This analysis yields group classification functions and posterior probabilities of classification of each subject to a particular group. In addition, a forward stepwise linear discriminant analysis was used on the total sample of 142 subjects (program 7M of the BMDP Dynamic, version 7, statistical package, Los Angeles, Calif., 1992) to derive a single subset of predictors. The default F-values of the program were used (F-to-add-a-predictor=4.0, F-to-remove-a-predictor=3.996). The input predictors for that analysis were $z_{ij}^O$ values from 271 sensor pairs which showed a highly significant group effect in an ANOVA (P<0.001, F-test). This was done in an effort to reduce the large predictor space consisting of 30,628 values.

Genetic Algorithm (GA)

A major objective of this example was to identify successful predictor subsets from a very large space. A brute-force approach in identifying all such subsets would be computationally deterring even for more than a few predictors, given the large size of the predictor set (N=30,628). For this reason, a GA was used to reduce computational time and optimize our search, as follows. An initial subset of a certain number of $z_{ij}^O$ predictors (out of the 30,628 available) was chosen randomly, and a micro-GA of population size=5 and uniform crossover was let to run for 24 hours. If, during the search, the fitness function solution was constant for $2 \times 10^5$ generations, a new random subset was chosen and the operation repeated. Practically, a GA abides to the natural selection law of "survival of the fittest". This way, characteristics that improve an evaluation function (classification in this case) are maintained, whereas the ones that do not are discarded.

Statistical Analyses of the $1^{st}$ Sample.

These analyses had two objectives, namely (i) to test the hypothesis that the number of good predictor subsets exceed that expected by chance, and (ii) to generate classification functions for the purpose of cross-validation with the $2^{nd}$ sample.

With respect to chance outcomes, given M subjects belonging to L groups, and subsets of the same size of k predictors out of N (=30,628) possible, the expected number s of subsets that would give 100% correct classification of each subject to its group by chance is $$s = Q\left(\frac{1}{L}\right)^M, \quad Q = \frac{N!}{k!(N-k)!}$$

For the analysis using an exhaustive search, k=2, L=3, M=17 (6 patients with AD, 3 subjects with CA, and 8 matched HC) were selected to perform a linear discriminant analysis using the robust leave-one-out method. A 100% correct classification of every subject to its corresponding group was required to retain a specific subset.

Linear Discriminant Classification Analysis: External Cross-Validation

The linear discriminant analysis yields classification functions for each group which are then used to classify individual subjects to a group. For the external cross-validation, classification functions derived from the $1^{st}$ sample were used to classify subjects from the $2^{nd}$ sample. For that purpose classification functions were used that gave 100% correct classification for the $1^{st}$ sample and applied them to the $2^{nd}$ sample.

Results $1^{st}$ Sample (52 Subjects, 6 Groups): Initial Analyses

First, a statistically significant Group effect on $z_{ij}^O$ (P<0.05, F test, ANCOVA) was found in 18% of sensor pairs. Next, a linear discriminant classification analysis (using GA) was carried out on subsets of $z_{ij}^O$ to find out whether individual subjects can be successfully classified to their respective groups. Indeed, many (in the thousands) such subsets of $z_{ij}^O$ predictors that classified each one of the 52 subjects 100% correctly were found. (The exact number of all such subsets is practically impossible to be determined.) An example is shown in FIG. 10. In many cases, successful subsets yielded not only 100% correct classification but also high (e.g., >0.98) posterior probabilities of correct classification of each subject to its group.

Since many $z_{ij}^O$ subsets are possible, it is useful to know whether the number of successful subsets exceeds that expected by chance. This number is typically very large and depends on the number of actual predictors, k, in a subset, the ensemble size of all possible $z_{ij}^O$ predictors (N=30,628), the number of groups, and the number of subjects to be classified. We investigated this problem in two tractable ways. In the first analysis, we performed an exhaustive search on a smaller sub-sample of the data using just 2 predictors (see Methods). This exhaustive assessment yielded 560 subsets with 100% correct classification (using the robust leave-one-out method), as compared to ~4 sets (3.63 to be exact) expected by chance. These proportions differ significantly (binomial theorem, normal deviate z=23.4, P<$10^{-50}$), indicating an excess (above chance) of good sets. In the second analysis, we used the whole $1^{st}$ sample of 52 subjects using 10 predictors, for which an exhaustive search would be infeasible. The expected number of subsets yielding 100% correct classification by chance is essentially zero (0.0069 to be exact). However, our discriminant classification program yielded 79 sets with 100% correct classification after running for a while. Although we cannot calculate the exact proportion of good sets in our data (since an exhaustive search is not feasible), this proportion already exceeds appreciably the chance expectation (z=8.78, P<$10^{-50}$).

2nd Consecutive Sample (46 subjects, 5 Groups): External Cross-Validation

In order to evaluate the robustness of this analysis and its potential as a useful clinical test, data from 46 subjects were processed during a subsequent period of time, following the $1^{st}$ sample. Specifically, an answer was sought as to whether the results of the analysis of the $2^{nd}$ sample were congruent with those of the $1^{st}$ sample with respect to (a) the distribution of the group effect assessed by ANCOVA on individual $z_{ij}^O$ of sensor pairs (N=30,628), and (b) the classification outcomes of the $2^{nd}$ sample based on classification functions derived from the $1^{st}$ sample (external cross-validation). With respect to the former, a statistically significant Group effect on $z_{ij}^O$ ($P<0.05$, F test, ANCOVA) was found in 11% of sensor pairs, as compared to 18% in the $1^{st}$ sample; the distribution of this effect among sensor pairs was highly congruent in the two samples ($P<10^{-11}$, $\chi^2$ test). And with respect to the latter, many of the $z_{ij}^O$ subsets which had given 100% classification in the $1^{st}$ sample also gave excellent classification scores (>90%, in the thousands) when classification functions calculated from the $1^{st}$ sample were applied to the $2^{nd}$ sample. These results underscore the similarity of the two samples and document the occurrence of excellent external cross-validation results.

Total Current Sample (142 Subjects, 7 Groups).

Data from 44 additional subjects have been analyzed for a total current sample of 142 subjects (7 groups). Many $z_{ij}^O$ predictor subsets were identified yielding 100% correct classification of every subject to its respective group. The number of such subsets was in the thousands (for 20 predictors), and even as few as 16 $z_{ij}^O$ predictors would give 100% correct classification results. It is also noteworthy that the posterior probabilities of subject classification were >0.95 in most cases, underscoring the power of this approach. Finally, a stepwise discriminant analysis (see Methods) yielded a subset of 12 $z_{ij}^O$ predictors which classified correctly 86.6% of the 142 subjects to their respective groups. Two cross-validation results were also obtained with this set. First, a jackknifed classification obtained by the leave-one-out method gave 78.9% correct classification. Second, the program was run 10 times using 80% of the data (randomly selected) for calculating the classification functions by which to predict the Group assignment of the remaining 20% of the subjects. The average correct classification was 86.4% (range: 79.3-93.8%), and the average correct jackknifed classification was 77% (range: 72.1-83.6%). These findings show that a high percentage of correct classification can be obtained robustly.

Discussion

The mechanisms for weak local cortical synchronization may rely on recurrent collaterals of pyramidal tract cells and specific parvalbumin-immunoreactive thalamocortical neurons, whereas calbindin-immunoreactive thalamocortical neurons could be responsible for larger-scale, multifocal cortical synchronization. The findings suggest that fine-grain synchronicity may be a fundamental aspect of cortical function that can be differentially disrupted by different disease processes, yielding a disease-specific signature.

A different issue concerns the specific subsets of zero-lag partial correlations that yield high classification rates. These cannot be found by exhaustive search, given the large space of 30,628 values available and the combinatorial nature of the subsets problem. Instead, a few different approaches were adopted in an effort to identify and evaluate such "good" subsets. First, we used classical statistics in applying a stepwise linear discriminant analysis to identify a single subset of predictors. Since the whole set is very large, we reduced it by first carrying out an analysis of variance with the disease ("Group") as a fixed factor, and then performing the stepwise linear discriminant analysis on 271 (out of 30,628) predictors which showed highly significant Group effect. This analysis yielded a set consisting of 12 predictors with high classification rates in standard reclassification analysis as well as in jackknifed leave-one-out classification and in 80/20% random split. However, like any stepwise procedure, the stepwise linear discriminant analysis relies on specific criteria for entering and/or removing predictors from the equation at each step, and these criteria can have a major influence on the outcome, in addition to the direction of stepping (forward or backward). This analysis, although useful, may not be optimally suited to our specific application. For that purpose, a first attempt to identify ideal (100% classification) predictor subsets by brute force was made, i.e. by searching within the entire combinatorial predictor subset space. We placed an emphasis on small subset sizes (<20) to avoid overfitting. Our initial analyses using random search did not produce any interesting result after running the program for several days. Therefore, a genetic search algorithm was implemented to quickly locate ideal sets. Indeed, this algorithm yielded a good number of such subsets within a day. This number exceeded that expected by chance, as the following was found out (a) in an exhaustive search of data from a few diseases and few predictors, and (b) in a larger sample where the number of ideal predictor subsets exceeded that of chance, although the exact number of such subsets could not be determined. The next step was to evaluate the power of such ideal predictor subsets to classify new subjects in an external cross-validation scheme. By focusing the genetic algorithm on that problem, thousands of subsets were identified yielding excellent cross-validation rates (>90%; hundreds >95%). Due to the large search space, the exact number of such subsets cannot be known.

In summary, these results demonstrate that (a) adequate information exists in the zero-lag partial correlations to differentiate brain disease states, (b) this information can be successfully extracted using linear discriminant analysis, (c) the results exceed those expected by chance alone, and (d) the results are robust and, to a good extent, cross-validated. It should be made clear that such studies, at whatever stage, are always evolving, since the addition of new study subjects and new disease groups will inevitably necessitate an updating of the predictor subsets and associated classification functions. In addition, other classification methods (e.g. based on support vector machine) could be tried and/or developed to improve classification outcome. Finally, it should be mentioned that, although the analyses described above were applied on 7 groups, they can also be applied, in general, on any pair of groups to serve, for example, as a screening test (healthy controls vs. all patients) or as a more specific aid in differential diagnosis between particular brain disorders (e.g. MS vs. MS-mimetic disorders, etc.).

Additional Examples

Neuronal activity in the brain produces both a magnetic signal and an electrical signal. A magnetic signal corresponding to the brain can be detected using a magnetoencephalography (MEG) sensor and an electrical signal can be detected using an electroencephalography (EEG) sensor. As used herein, an electromagnetic sensor can be used to detect either an electrical signal or a magnetic signal.

In addition to MEG and EEG sensors, other modalities can be used to collect temporal data from the brain. For example, a functional magnetic resonance imaging (fMRI) is a modality that provides data corresponding to the behavior of electron spins within the body during a particular activity. Positron emission tomography (PET) is another modality that detects gamma ray radiation emitted from radioactive substances introduced into the body. Computed tomography (CT) is another modality that generates data based on scanned X-rays. Data from such modalities can be used to refine the estimate generated by the subject matter described herein.

Figure 11:
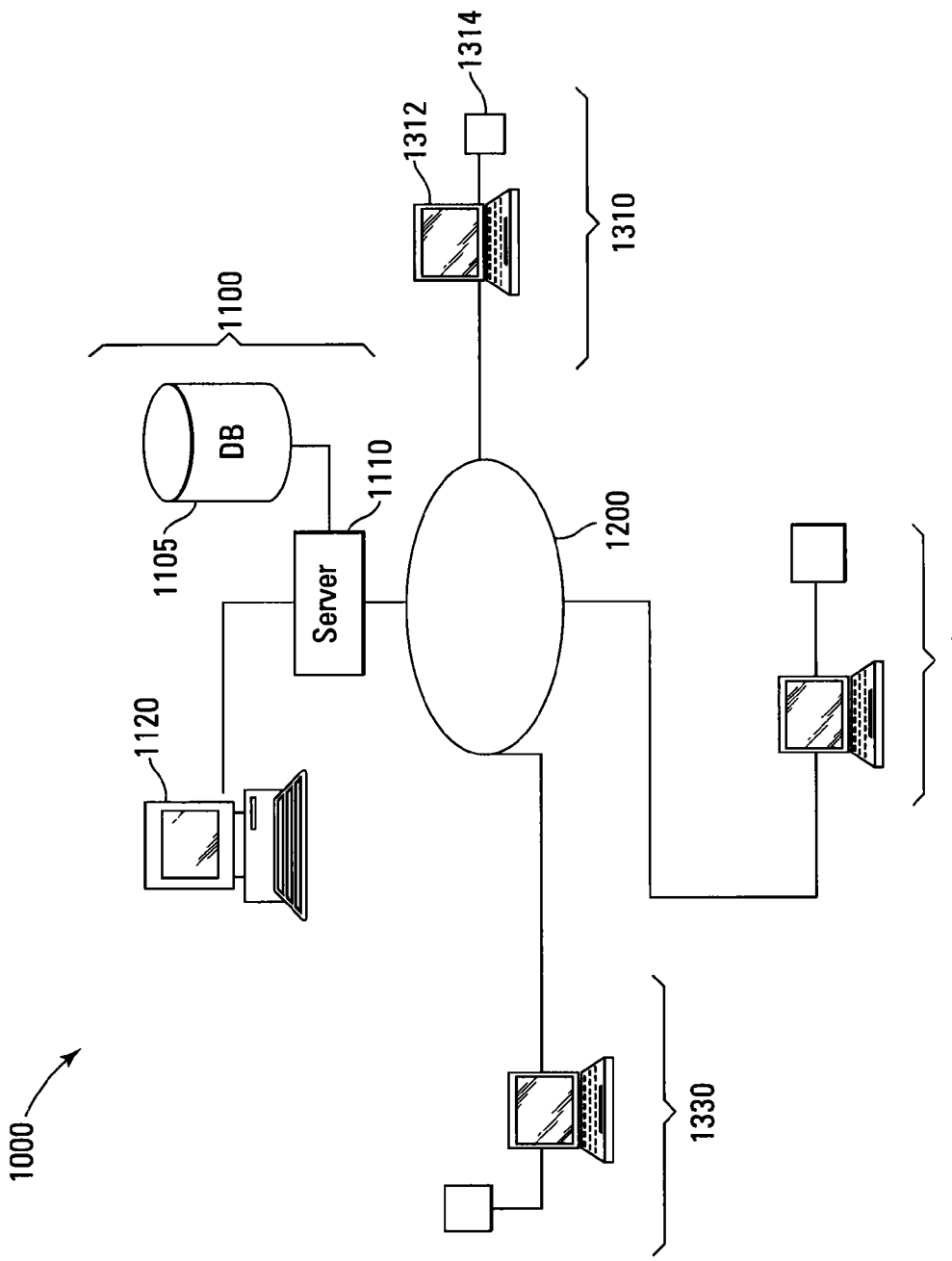
FIG. 11 illustrates a network implemented example of the present subject matter.

In one example, the present subject matter includes a system and business method for generating data for dynamic functions. FIG. 11 illustrates system 1000 including central server 1100 and communication network 1200. Central server 1100 includes server 1110 coupled to database 1105 and terminal 1120. Server 1110 executes and algorithm based on instructions stored in a memory or other storage facility such as database 1105. Database 1105 can include magnetic, optical or other data storage device. Terminal 1120 provides an input device as well as an output device to allow operation and control of system 1000.

In FIG. 11, client sites 1310, 1320 and 1330 are representative of clinics or health care facilities that generate data according to the present subject matter. Three such client sites are illustrated however, more or fewer are also contemplated. Data, for example, is generated at client site 1310 by sensor 1314 under control of local processor 1312. The data includes a time series corresponding to brain activity. The time series is captured using local processor 1312 in communication with sensor 1314 which can include an array of superconducting quantum interference devices (SQUIDS). Time series data stored at local processor 1312 is communicated to central server 1100 using communication network 1200. Communication network 1200 can include a wired or wireless network, examples of which include an Ethernet network, a local area network (LAN), a wide area network (WAN) such as the Internet, and a public switched telephone network (PSTN).

The central server can include a processor coupled to a memory and having instructions stored thereon to execute an algorithm as described herein. The central server can include more than one processor which can be distributed across multiple locations. Persons skilled in the art will readily appreciate that the processor of the central server can be embodied by any suitable processor including, without limitation, a RISC or CISC microprocessor, a microcontroller, a microcomputer, a FPGA, an ASIC, an analog processor circuit, a quantum computer, or a biological processor, for example, and can include single or multiple processing units. The processor can also be of a type that operates in batch mode or real-time mode.

In one example, client sites are licensed or enrolled on a subscription basis. For a fee, the central server executes an algorithm to generate an estimate of dynamic brain activity based on the time series. In one example, the central server provides a report which includes the estimate. The estimate can be rendered in an alphanumerical or graphical format.

Figure 12A:
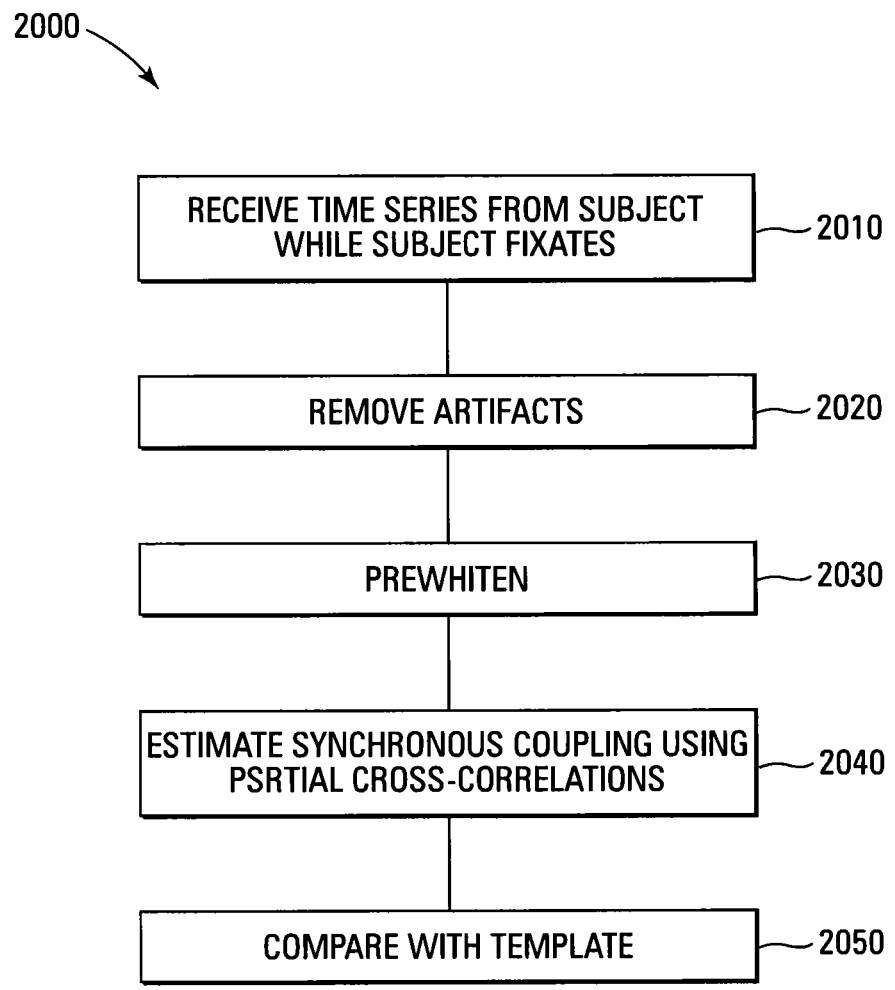
FIGS. 12A and 12B illustrate methods corresponding to examples of analyzing a subject according to various aspects of the invention.

FIG. 12A illustrates method 2000 performed by one example of the present subject matter. At 2010, time series data is received. The time series data is generated while the subject is performing an eyes-open task involving only nominal stimulation and motor activity, such as visually fixating on a target. This type of eyes-open task causes the subject's brain to remain in a generally idle state.

The time series data can be received and stored by a processor some time after the data is generated by a sensor or array of sensors. At 2020, artifacts in the data are removed. Artifacts can include those produced by breathing, cardiac artifacts, physical movement or other artifacts. At 2030, the data is prewhitened by, for example, converting the MEG time series to a stationary, white noise series. At 2040, an estimate of synchronous coupling is generated by calculating partial cross correlations. The estimate is then compared with a template at 2050.

In one example, the template is generated based on stored data for the particular subject under review. In one example, the template is generated based on stored data derived from a plurality of different subjects. An analysis can be performed by comparing the subject data with a template, and, in one example, the template is modified with the results for that particular subject. In another example, the template is modified in a batch mode after having compiled a number of subjects over a period of time.

Figure 12B:
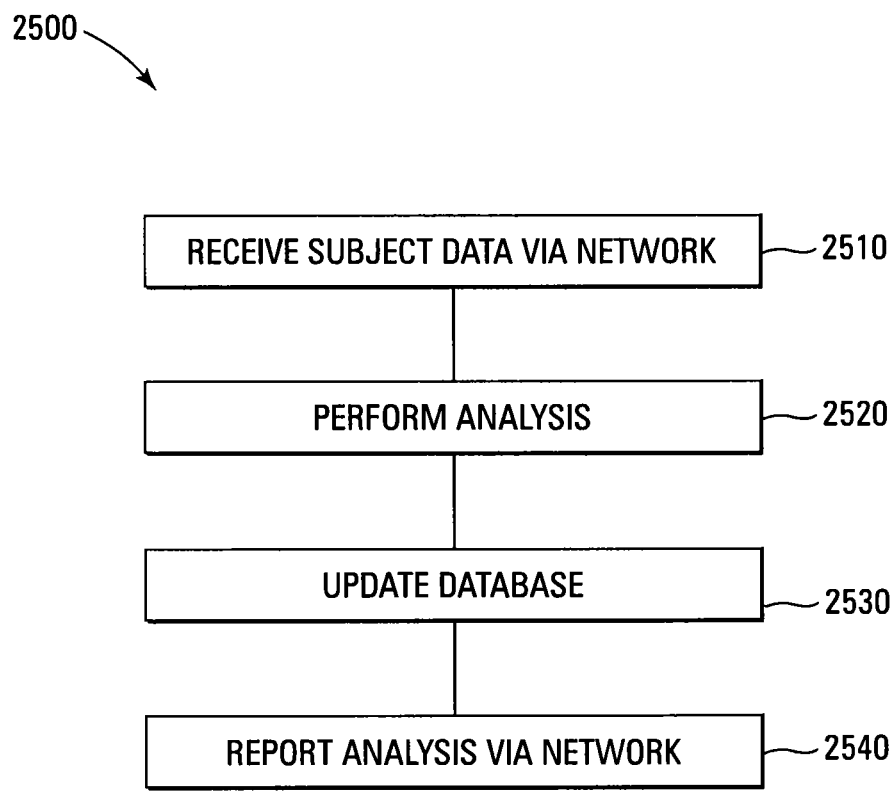

FIG. 12B illustrates method 2500 suitable for implementation using a network such as that shown in FIG. 11. At 2510, the subject data is received over an internet connection. In one example, the subject data includes the MEG time series data. At 2520, analysis is performed using, for example, server 1100. At 2530, database 1105 is updated with the information corresponding to the particular subject. At 2540, the results, which can include analysis of the data, are reported to the client site using the network.

In one example, the central server provides a screening report that provides an indication of normalcy. Such a binary report, showing normal or a departure from normal, can be used as a threshold determination by the client site as to brain condition.

In one example, the central server can provide a diagnosis that includes a classification based on a comparison with a database. The database includes stored data corresponding to a number of previously analyzed time series. In addition, the database can be updated with new data as client time series data is received. In one example, the client site can request and receive trend data that includes a comparison of earlier time series data for a particular brain with later time series data. In forming a diagnosis, the present subject matter differentiates among a plurality of disease states.

The database can provide data for generating a template or model for analysis of a particular subject. A template can, for example, correspond with a particular disease or other neuronal condition or with a normal brain.

In one example, the central server provides feedback to allow monitoring of subject progress. In particular, disease progression and therapy progression can be monitored by generating multiple estimates over a period of time. In addition, estimates of neuronal synchronicity can be generated during a drug trial. Safety and efficacy of a therapy regimen can be evaluated by using the present subject matter to monitor a drug trial.

A computer implemented algorithm can be implemented in software instructions stored in a memory. Portions of the software can be executed at a client site and the central server.

In one example, the estimate is determined, in part, as a function of the age of the subject. Age-adjusted data can be stored in the database. Other data can also be stored in the database and used for discriminating, including, for example, known medical conditions or therapy regimens.

As the database evolves, it is expected that particular variables will be strongly correlated with particular disease conditions. As such, these particular variables can be weighted differently to more quickly and accurately distinguish between different conditions. In one example, subjects can be classified using a subset of the calculated correlations as a predictor. For example, a linear discriminant classification analysis using the 'leave-one-out' method can be used. In one example, six correlations are adequate to correctly classify subjects (100% correct) with posterior probability of 1.0.

In addition, it is believed that embodiments the present invention may have utility for discerning the veracity of a subject. In the form of a lie detector, data is collected from the subject coincident with an assertion to be tested. In addition, it is believed that the other embodiments of the present invention may have utility for analyzing or testing intelligence. As such, particular markers may be identified to coincide with a particular intelligence grade.

Certain embodiments of the present invention can provide an objective test to enhance diagnostic accuracy, advance the recognition of AD (and other conditions) into a presymptomatic stage, and serve as a monitor for therapy.

The number of sensors used to capture the time series can be adjusted to any value and in one example the number is reduced to a value sufficient to reach a conclusion of interest. For instance, one example uses a reduced set of sensors, (i.e. six or fewer) to generate a meaningfully time series sufficient to reach a conclusion as to a particular neurological condition.

The present subject matter can be used with subjects having a variety of brain conditions. Some examples of brain conditions or diseases that can be identified, diagnosed, or monitored with the present subject matter include: a person under the influence of alcohol or a drug, a neurological disease or condition, multiple sclerosis, bipolar disorder, traumatic brain injury, Parkinson's disease, depression, autoimmune disorder, neurodegenerative disorders or diseases, pain, and diseases that affect the central nervous system (CNS). In addition to identifying the effects of alcohol or other drug, the present subject matter can be used to diagnose chronic alcoholism or fetal alcohol syndrome. For example, embodiments of the present invention can be used to monitor day-to-day changes in brain condition while a subject is consuming alcohol or using a drug.

In general, embodiments of the present invention can be used to diagnose a condition or disease using a stored template, differentiate between a number of different conditions or diseases, and monitor a subject over a period of time.

In one example, the present subject matter includes hierarchical clustering of magnetoencephalographic (MEG) data. Data can be acquired from 248 axial gradiometers while 10 healthy subjects fixate on a spot for 45 s. The data is preprocessed to remove cardiac or eye blink artifacts.

Hierarchical clustering of synchronous dynamic brain networks using stationary MEG data, free of cardiac or eye blink artifacts can be visualized. Data is collected from 248 axial gradiometers (0.1-400 Hz, sampled @ 1017 Hz, Magnes 3600 WH, 4-D Neuroimaging, San Diego, Calif.) while 10 healthy subjects fixate on a spot of light for 45 s. After prewhitening the time series by fitting an AutoRegressive Integrative Moving Average (ARIMA) model and taking the residuals, all pairwise, zero-lag, partial cross correlations (N=30,628) are calculated, thus providing estimates of the strength and sign (positive, negative) of direct synchronous coupling between neuronal populations at 1 ms temporal resolution. A hierarchical additive tree clustering analysis is used and distances derived from the mean partial correlation for each sensor-sensor pair. Partitioning the tree demonstrates robust patterns of clustering across subjects. Interactions among the clusters are estimated using the mean partial correlation between the sensors of each pairwise combination of clusters. Plots of the clusters can reveal a rich complexity in composition and interaction. The present subject matter can be used for functional grouping of interacting neuronal populations, which can assess various disease groups or conditions. Some embodiments of the present invention can include linear discriminant classification analysis of synchronous neural interactions assessed by magnetoencephalography (MEG).

AD is a representative example for consideration. MEG can be used to assess the dynamic status of the brain in 3 groups of elderly subjects: normal (N=6, 72.3+/−2.4 y, mean+/−SEM), subjects with mild cognitive impairment (N=6, 76.9+/−2.5), and subjects with AD (N=6, 76.8+/−1.6). Data can be acquired from 248 axial gradiometers (0.1-400 Hz, sampled @ 1017 Hz, Magnes 3600 WH; 4-D Neuroimaging, San Diego, Calif.) while subjects fixate on a spot for 45 s. The data is preprocessed to remove cardiac or eye blink artifacts. After prewhitening the time series by fitting an AutoRegressive Integrative Moving Average (ARIMA) model and taking the residuals, all pairwise, zero-lag, partial cross correlations (N=30,628) are calculated, thus providing estimates of the strength and sign (positive, negative) of direct synchronous coupling between neuronal populations at 1 ms temporal resolution. The subjects can be classified in the 3 groups using small subsets of these correlations as predictors. For example, linear discriminant classification analysis using the robust leave-one-out method can be used. Predictor subsets with, for example, 6 correlations are adequate in correctly classifying all subjects to their respective groups (i.e., 100% correct classification) with posterior probability of 1.0. The present subject matter can serve as a dynamic test for brain function.

Figure 13:
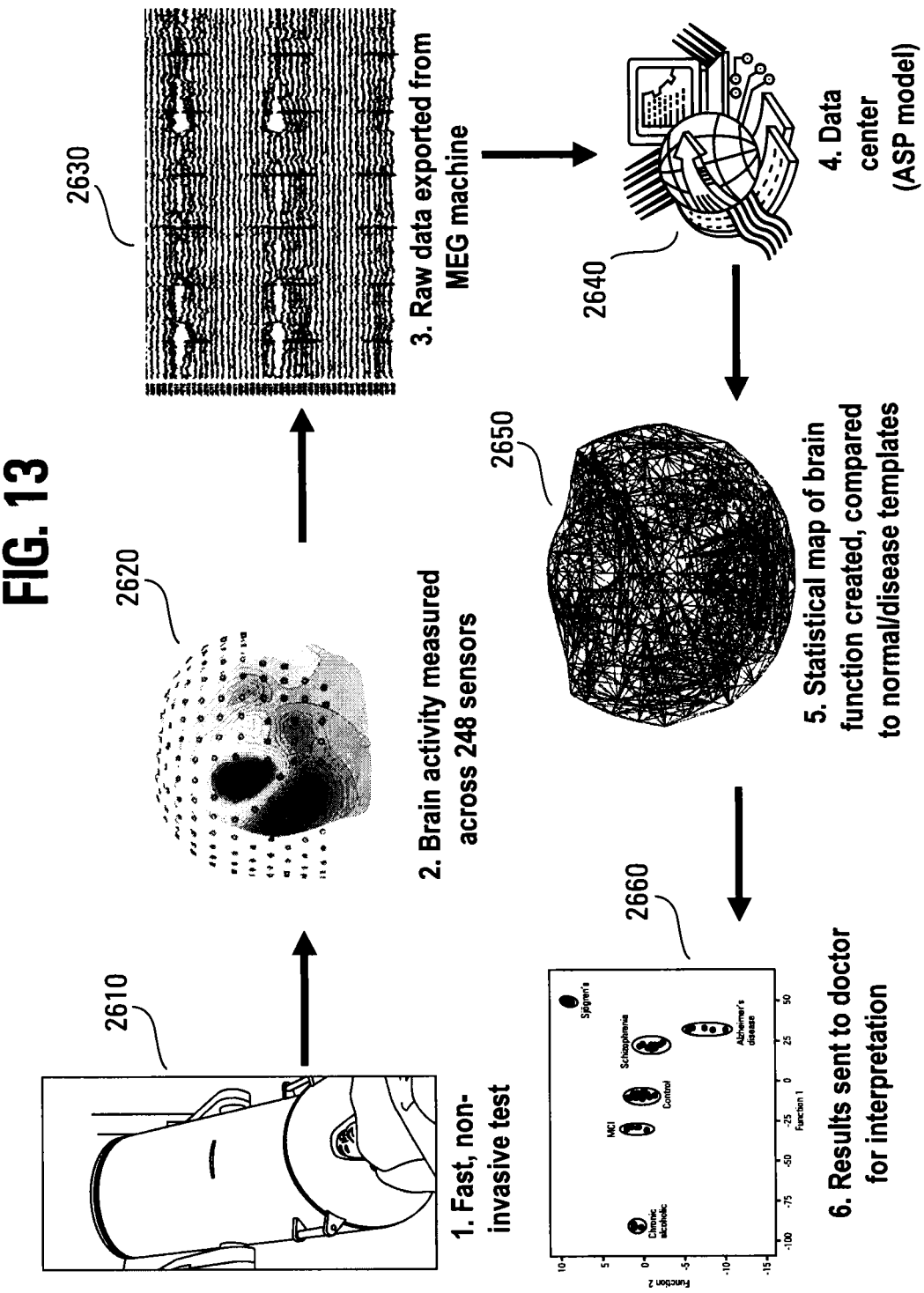
FIG. 13 is a diagram illustrating an overview of a process of analyzing a subject according to one aspect of the invention.

FIG. 13 illustrates an overview of a process according to one embodiment. At 2610, an electromagnetic measurement apparatus, such as a MEG conducts a non-invasive test of a subject. As described above, in one embodiment, the subject is instructed to perform an eyes-open fixed visual stimulus task to place the subject's brain in an eyes-open idle state. At 2620, the electromagnetic measurement apparatus gathers time series data of the patient's brain. In one embodiment, the data is sampled at a minimum sampling frequency of 1 kHz corresponding to a time resolution of 1 ms or better. This relatively fast sampling rate and temporal resolution generally corresponds to the rate at which neural activity occurs in the subject's brain. The data is gathered by a multiplicity of sensors spatially distributed around the subject's brain.

At 2630, a set of time series, each of which has been gathered by a corresponding sensor is transmitted or otherwise delivered to a data center which has data processing and, optionally, data storage facilities. At 2640, the data is received at the data center. The processing occurring at 2650 produces a dynamic model that represents statistically-independent temporal measures among neural populations of the subject. The temporal measures can be, for example, time-wise related sensed signals detected by various sensors. These signals may coincide based on the sampling intervals such that they have coincidence without lag (i.e., simultaneous, or asynchronous by less than a detectable amount). Alternatively, the temporal measures can be based on non-synchronous, but nevertheless temporally-related signals, such as signals interacting within a certain time window (e.g., a 50 ms window).

The temporal measures among neural populations can relate to pairs of sensors, or to other groupings such as groups of 3 or more sensors that demonstrate a temporal interaction with one another.

The statistical independence of the temporal measures relates to the apparent interaction between the pairings or other groupings of sensors taking into account the other variables. One type of computation that can achieve statistically independent temporal measures is the partial cross correlations described in the above examples. However, other approaches may be applicable in certain applications within the scope and spirit of the invention. For instance, the use of residuals may produce statistical independence of groupings of temporal measures.

As discussed above, the dynamic nature of the model means that the model of temporal measures is represented as a function of time, such that it can be different for each sampling period. Notably, the dynamic model of temporal measures can be regarded in one sense as a network of interacting spatial nodes, and not merely a network having nodes in only a structural configuration. While the above examples provide spatial representations of the "brain maps," the data can be represented in any suitable form within the scope and spirit of the invention.

As described above, certain advantages may be realized in processing the raw measurement data to remove artifacts and/or to pre-whiten each of the time series to produce signals having a characteristic of stationarity of mean, variance, and autocorrelation. This step of pre-whitening further contributes to the statistical independence of the temporal measures that are to be computed.

Once the dynamic model is computed, it can be further processed to simplify or filter the model. One type of filtering is the use of a threshold function to remove temporal measures having a relatively weaker magnitude, and leaving only the strong temporal measures to utilize for analyzing the subject's brain.

In one embodiment, temporal measures are analyzed for covariance with one or more external property of the subject such as, for example, age, race, or neuropsychological capacities.

At 2650, the data center compares the dynamic model of temporal measures with one or more templates classified according to various brain conditions. Templates can be regarded in one sense are validated models of neurophysiologic conditions. In one type of embodiment, templates are each based on a group of previously-evaluated subjects that share a common neurophysiologic characteristic, such as a disease or disability. In this embodiment, the templates are validated in that there is strong statistical correlation among indicators corresponding to the condition for the group of subject upon which the template is based.

Each template may itself be a dynamic model of temporal measures, or a subset of such a dynamic model. A template may be stored as a data record, or may be represented as an algorithm or function that, when "compared" to the subject's dynamic model, modifies the dynamic model to achieve the result of the comparison. In one sense, a template is a classification function. In one example embodiment, a template is in the form of a data mask with weighted taps.

As in the examples above, the template can be limited to only a selected subset of groupings (e.g., pairs) of temporal measures, with the remaining temporal measures omitted as being irrelevant to the condition to which that template corresponds. In this regime, different templates may have different groupings of relevant temporal measures to the corresponding condition or disorder.

When the dynamic model (or subsets thereof) of patient data is compared against one or more templates different subsets of the dynamic model may be compared against each different template. Thus, for a template that represents pairs A, B and E of correlated sensor data (identified based on their spatial positioning), only pairs A, B, and E of the dynamic model of temporal measures taken from the subject needs to be compared. For a different template in which pairs C, D, and E are relevant, only those pairs taken from the dynamic model may be used. The resulting comparison can be scored, or otherwise represent a degree of correlation. Alternatively, the comparison can produce a binary (yes/no) result.

In one aspect of the invention, the dynamic model of the temporal measures of the subject is stored, and later used to compare against more recent measurements of the same subject. This approach may be useful for tracking disease progression or evaluating effectiveness of a particular therapy. In a related embodiment, a template is made based on different sets of data from the same subject, and the template is used for tracking of the patient's condition over time.

At 2660, the system generates a report, which may include a graphical representation of the dynamic model of the patient, mapped to 2-d or 3-d space for visualization similar to the output illustrated in FIG. 3 or 10.

Figure 14:
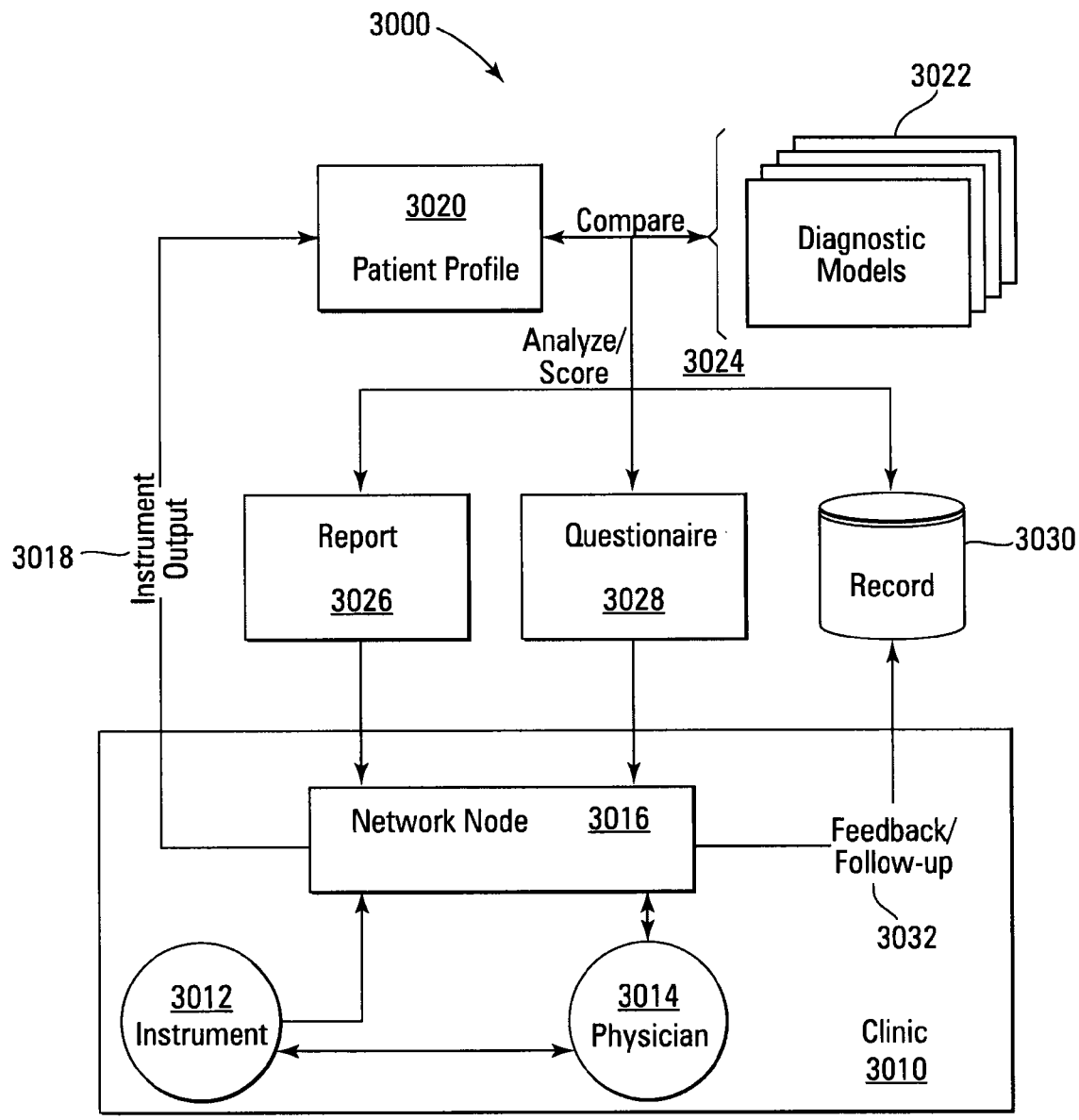
FIG. 14 is an information flow diagram illustrating exchange of information in a system according to one aspect of the invention.

FIG. 14 is a diagram illustrating information flow 3000 according to one aspect of the invention. Clinic 3010 includes a subject-measuring instrument 3012, and physician or lab technician 3014. Network node 3016 facilitates communication with remote nodes. In one embodiment, the network node 3016 includes a computer system, such as a PC, having a network interface. Network node 3016 can also facilitate an operator interface between physician 3014 and the instrument 3012.

In one embodiment, measurements are made by instrument 3012 and stored locally on network node 3016 prior to transmission. Network node is then instructed to transmit instrument output 3018 to an external system for analysis. The system creates a patient profile 3020 corresponding to instrument output 3018 in association with a patient ID. The system processes information from patient profile 3020, such as the instrument output 3018, according to any of the analysis techniques described above, and including comparing information based on the instrument output against diagnostic models 3022. In one embodiment, diagnostic models 3022 are analogous to the templates described above.

The result 3024 of the comparison can be used to generate report 3026 for delivery to clinic 3010 via network node 3016. Report 3026 can include the result 3024 of the comparison, along with an automatically-generated discussion and graphical output depicting the result 3024. Additionally, the result 3024 can be associated with questionnaire 3028, also for delivery to clinic 3010 via network node 3016. Questionnaire 3028 can be filled out by physician 3014 to provide additional information of interest about the patient, the testing environment, therapies, manual diagnoses, and the like. The filled-out questionnaire is then provided as feedback/follow-up 3032 to be stored in data store 3030 in association with the patient ID, the report 3026, the result 3024, and the instrument output 3018.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first,"

"second," and "third," etc. are used merely as labels, and are not intended to impose numerical requirements on their objects.

The Abstract of the Disclosure is provided to comply with certain national requirements for an abstract that will allow the reader to quickly ascertain the nature of the technical disclosure. It is submitted with the understanding that it will not be used to interpret or limit the scope or meaning of the claims. In addition, in the foregoing Detailed Description, various features may be grouped together to streamline the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus the following claims are hereby incorporated into the Detailed Description, with each claim standing on its own as a separate embodiment.

What is claimed is:

1. A system for classifying neurophysiologic activity of a first subject, the system comprising:
   a data input configured to receive brain activity data corresponding to an idle state of the brain of the first subject, the brain activity data representing a time series of neurophysiologic activity acquired by a sensor system arranged to detect spatial and temporal neural signaling in the subject utilizing magnetic fields produced in a multiplicity of brain regions; and
   a processor communicatively coupled to the data input, and programmed to:
      process each set of brain activity data to produce a corresponding dynamic model of neural activity representing time-dependent coupling between neural populations of the brain of the first subject, including:
         processing the brain activity data to produce a prewhitened time series;
         computing partial cross correlations of the prewhitened time series to produce estimates of strength and sign of signaling between groups of the multiplicity of brain regions representing interactions of neural populations, based on an analysis of covariance of at least one type of partial cross correlations selected from the group consisting of: (a) positive partial cross correlations of the partial cross correlations of the prewhitened time series, and (b) negative partial cross correlations of the partial cross correlations of the prewhitened time series;
      performing a classification of the partial cross correlations to produce a measure of correlation of the brain activity data to validated reference data corresponding to a plurality of different neurophysiologic conditions.

2. The system of claim 1, wherein the plurality of different neurophysiologic conditions includes at least two conditions selected from the group consisting of: a normal condition, Alzheimer's Disease, pre-dementia syndrome, mild cognitive impairment, schizophrenia, Sjögren's Syndrome, alcoholism, alcohol impairment, fetal alcohol syndrome, multiple sclerosis, Parkinson's Disease, bipolar disorder, traumatic brain injury, depression, an autoimmune disorder, a neurodegenerative disorder, pain, a disease affecting the central nervous system, or any combination thereof.

3. The system of claim 1, wherein the processor is programmed to apply an autoregressive integrative moving average-based algorithm to produce the prewhitened time series.

4. The system of claim 1, wherein the partial cross correlations are computed to produce estimates of strength and sign of direct short-term signaling between the pairs of the multiplicity of sensors occurring within time windows of about 50 milliseconds.

5. The system of claim 1, wherein the partial cross correlations are computed to produce estimates of strength and sign of substantially simultaneous signaling between the pairs of the multiplicity of sensors within a time window of 1 millisecond.

6. The system of claim 1, wherein the processor is further programmed to apply a thresholding function to the estimates of strength and sign of signaling between pairs of the multiplicity of sensors to produce the first dynamic model of neural activity.

7. The system of claim 1, wherein the processor is programmed to determine a relevant subset of the partial cross correlations that consists of certain partial cross correlations relevant for performing the classification.

8. The system of claim 7, wherein the processor is programmed to determine the relevant subset of the partial cross correlations utilizing a leave-one-out algorithm wherein 100% classification is required for any one of the partial cross correlations to be deemed relevant.

9. The system of claim 7, wherein the processor is programmed to determine the relevant subset of the partial cross correlations utilizing a genetic algorithm.

10. The system of claim 1, wherein the processor is programmed to develop a neurophysiologic template based on the classification.

11. The system of claim 1, wherein the dynamic model of neural activity is a first dynamic brain model of the first subject based on the brain activity data, which is taken at a first time, and wherein system is further configured to produce a different dynamic model of neural activity based on a second dynamic brain model of the first subject obtained from a second set of brain activity data taken at a second time that is different from the first time; and
   wherein the processor is programmed to analyze a potential change in neurophysiology of the first subject between the first time and the second time based on a comparison of the first dynamic brain model and the second dynamic brain model.

12. The system of claim 1, wherein the groups of the multiplicity of brain regions between which the estimates of strength and sign of the signaling are computed are pairs of brain regions, such that the interactions of neural populations are pair-wise interactions of neural populations.

13. The system of claim 1, wherein the processor is programmed to produce the dynamic model based on the brain activity data including data representing the time series of neurophysiologic activity-corresponding to less than or equal to one minute of eye fixation activity.

14. The system of claim 1, wherein the sensor system arranged to detect spatial and temporal neural signaling in the subject utilizing magnetic fields produced in a multiplicity of brain regions is a magnetoencephalogram instrument having a plurality of sensors arranged around the brain of the first subject, with each sensor gathering brain activity data from a corresponding one of the multiplicity of brain regions.

15. A non-transitory computer-readable medium comprising instructions that are adapted to cause a computer system to:
   receive sets of brain activity data corresponding to an idle state of the brain of a first subject, each set representing a time series of neurophysiologic activity acquired by a sensor system arranged to detect spatial and temporal neural signaling in the subject utilizing magnetic fields produced in a multiplicity of brain regions;

process each set of brain activity data to produce a corresponding dynamic model of neural activity representing time-dependent coupling between neural populations of the brain of the first subject, including:
  processing the brain activity data to produce a prewhitened time series;
  computing partial cross correlations of the prewhitened time series to produce estimates of strength and sign of signaling between groups of the multiplicity of brain regions representing interactions of neural populations, based on an analysis of covariance of at least one type of partial cross correlations selected from the group consisting of: (a) positive partial cross correlations of the partial cross correlations of the prewhitened time series, and (b) negative partial cross correlations of the partial cross correlations of the prewhitened time series; and
perform a classification of the partial cross correlations to produce a measure of correlation of the brain activity data to validated reference data corresponding to a plurality of different neurophysiologic conditions.

\* \* \* \* \*